US006583340B2

(12) United States Patent
Slabas et al.

(10) Patent No.: US 6,583,340 B2
(45) Date of Patent: Jun. 24, 2003

(54) DNA SEQUENCE ENCODING PLANT 2-ACYLTRANSFERASE

(75) Inventors: Antoni Ryszard Slabas, High Shincliffe (GB); Adrian Paul Brown, Whitley Bay (GB); Clare Louise Brough, Merryoaks (GB); Johannes Theodorus Maria Kroon, Chester-le-Street (GB)

(73) Assignee: Gene Shears Pty. Limited, North Ryde (AU)

( * ) Notice: Subject to any disclaimer, the term of this patent is extended or adjusted under 35 U.S.C. 154(b) by 286 days.

(21) Appl. No.: 08/818,581

(22) Filed: Mar. 14, 1997

(65) Prior Publication Data

US 2002/0007499 A1 Jan. 17, 2002

Related U.S. Application Data

(63) Continuation of application No. PCT/GB96/00306, filed on Feb. 9, 1996.

(30) Foreign Application Priority Data

Feb. 9, 1995 (GB) .............................. 9502468

(51) Int. Cl.⁷ .......................... A01H 5/00; C12N 15/82; C07H 21/04
(52) U.S. Cl. ...................... 800/306; 800/281; 800/298; 435/468; 435/419; 536/23.6
(58) Field of Search ................................ 800/281, 298, 800/306; 433/69.1, 468, 320.1, 471, 419, 430, 252.3; 536/23.6

(56) References Cited

U.S. PATENT DOCUMENTS

| 5,563,058 A | * 10/1996 | Davies et al. ............... 435/193 |
| 5,910,630 A | * 6/1999 | Davies ....................... 800/295 |
| 5,968,791 A | 10/1999 | Davies et al. |

FOREIGN PATENT DOCUMENTS

| EP | 0242246 | 11/1992 | |
| EP | 0344029 | 1/1997 | |
| WO | 9413814 | * 6/1994 | .......... C12N/15/54 |
| WO | WO9527791 | 10/1995 | |
| WO | WO9609394 | 3/1996 | |

OTHER PUBLICATIONS

Taylor et al, Plant Physiol 109: 409–420, Oct. 1995.*
*Plant Science*, 67, 21–28 (1990); Bernerth and Frentzen.
*Chemical Abstracts*, Jul. 16, 1990, 113(3), No. 20895a, Bernerth et al.
*Plant Mol. Biol.* 29(2) 267–278, Oct. 1995; Brown A.P.
*Plant Mol. Biol.* 26 211–223 (1994); Brown et al.
*Plant Physiol*, 82, 813–820 (1986); Cao and Huang.
*Plant Physiol*, 94, 1199–1206 (1990); Cao.
*Lipid Analysis*, 2nd Edn. Pergamon Press, Toronto, Canada: 158–161 (1982); Christie.
*Molecular and General Genetics* 232 295–303 (1992); Coleman.
*European Journal of Biochemistry* 232(3) 806–810, Sep. 15, 1995; Hanke et al.
Plant Lipid Metab. [Pap. Int. Meet. Plant Lipids] 11th (1995), International Meeting on Plant Lipids, Paris, France, Jun. 26 to Jul. 1, 1994. 531–3 Hanke et al.
*Planta* 185 124–131 (1991); Hares et al.
*Chemical Abstracts*, Nov. 11, 1991, 115 No. 201740h; Hares et al.
*EMBO J.* 2(6) 987–995 (1983); Herrera–Estella et al.
*Nature* 303 209–213 (1983); Herrera–Estrella et al.
*Trends in Biotechnology*, Feb. 1987 (5), 40–47; Knauf.
*Plant Physiol.*, 109, 409–420 (1995), Lassner et al.
*Plant Physiol.*, 99 1711–1715 (1992): Laurent and Huang.
*Chemical Abstracts*, Mar. 2, 1992, 116(9), No. 79057u; Loehden et al.
*Plant Lipid Biochemistry*, Proceed. 9th Int. Symposium, 1990, 175–177; Lohden et al.
*Biological Abstracts*, 94 (1992), Abstract No. 136764; Loehden et al.
*Planta* 188(2) 215–224 (1992).
*J. Am. Oil Chem. Soc.*, 41 693–696 (1964); Luddy et al.
*Plant Cell Reports* 8 238–242 (1989); Moloney et al.
*J. Biol. Chem.* 268(29), Oct. 15, 1993: Nagiec et al. pp 22156–22163.
*Plant Physiol.*, 91, 1288–1295 (1989); Oo and Huang.
*Fat Science Technology*, 93(11), 417–418 (1991); Peterek et al.
*Biological Chemistry:* Pflanzliche Lipide; Abstract; 372(8), 539, Peterek et al.
*J. Am. Oil Chem. Soc.* 69(4) 355–358 (1992); Taylor et al.
*J. Am. Oil Chem. Soc.* 71(2) 163–167, Feb. 2, 1994; Taylor et al.
*Plant Physiol*, 109, 1389–1394 (1995); Taylor et al.
*Chemical Abstracts*, 119(19), (1993), Abstract No. 199618; Taylor et al.
*Inform* 3(4) 482, Apr. 1, 1992; Trani et al.
*Fat Science Technology*, 93(8) 288–290 (1991); Wolter et al.

* cited by examiner

Primary Examiner—Elizabeth F. McElwain
(74) Attorney, Agent, or Firm—John P. White; Cooper & Dunham LLP

(57) ABSTRACT

Plants, particularly transgenic plants, may be produced having a 2-acyltransferase enzyme from Limnanthes with an altered substrate specificity compared to the native enzyme. For example, oil seed rape (*Brassica napus*) may contain the 2-acyltransferase transgene derived from *Limnanthes douglasii* in order to produce trierucin. The cDNA sequence of *Limnanthes douglasii* 2-acyltransferase and its equivalents protein sequence are disclosed.

34 Claims, 21 Drawing Sheets

FIGURE 1

FINAL LIM SEQ (CB121) - Genes

Figure 8:

DNA sequence    1515 b.p.    GAATTCGCGGCC ... GGCCCCGAATTC    linear

```
  1 GAATTCGCGGCCGCTACCGGCCATTCTAATTTTATATCCAAACGCCCCTCCTCCATCTTCCTCGATTCATTTTCTCGATC   80
 81 TTTCATCTTTCCTACCATTCCTCTCTCTACACATTCTTTTACACTATACATCCTTAGAGCTTCTTCCCTCATCGTT     160
161 ATAGCCCGAGCTAAAGCTCC|ATG GCG ATC CCT GCA GCT TTC ATC GTA CCA ATA AGT CTT           223
  1                      M   A   I   P   A   A   F   I   V   P   I   S   L           14

224 CTT TTT TTC ATG TCA GGC CTC AAT TTC GTT ATT CAG GCA GCA GTC TTC TAT GTT CTT GTT   283
 15  L   F   F   M   S   G   L   N   F   V   I   Q   A   A   V   F   Y   V   L   V    34

284 CGC CCT ATT TCT AAG GAC ACA TAC AGA AGG ATC AAT ACG TTC GTG GCA GAA TTG TTG TGG   343
 35  R   P   I   S   K   D   T   Y   R   R   I   N   T   F   V   A   E   L   L   W    54

344 CTA GAA CTT GTA TGG GTC ATT GAT TGG ATG GCA GGC GTT AAG GTC CAA TTA TAT ACT GAT   403
 55  L   E   L   V   W   V   I   D   W   M   A   G   V   K   V   Q   L   Y   T   D    74

404 ACT GAG TCT TTC CGT CTA ATG CGT AAA GAA CAT GCA CTC TTA ATA TGC AAC CAC AGA ACT   463
 75  T   E   S   F   R   L   M   G   K   E   H   A   L   L   I   C   N   H   R   S    94

464 GAC ATT GAC TGG CTC ATT GGA TGG CTC CTA CCA CAG CGA TGC GGC TGC CTC AGT TCT TCA   523
 95  D   I   D   W   L   I   G   W   L   L   P   Q   R   C   G   C   L   S   S   S   114

524 ATA GCT GTT ATG AAG AAG TCA TCC AAA TTT CTC CCG GTA ATA GGT TGG TCT ATG TGG TTT   583
115  I   A   V   M   K   K   S   S   K   F   L   P   V   I   G   W   S   M   W   F   134

584 TCC GAA TAT CTC TTT CTG CAG AGG GCC AAA GAT GAA AAC ACT TTA AAG TCA GGT           643
135  S   E   Y   L   F   L   Q   R   A   K   D   E   N   T   L   K   S   G           154

644 CTC CAG CGG CTG AAT GAC TTC CCT AAG CCT TTT TGG TTA GCT CTG TTT GTG GAA GGA ACT   703
155  L   Q   R   L   N   D   F   P   K   P   F   W   L   A   L   F   V   E   G   T   174

704 CGT TTC ACC AAA GCA AAA CTT CTA GCT CCT GCT CAG CAG GAA TAT GCA GCC TCT GCA GGA TTA CCC   763
175  R   F   T   K   A   K   L   L   A   P   A   Q   Q   E   Y   A   A   S   A   G   L   P   194
```

FIGURE 1 (cont.)

```
764  GTG CCT CGA AAT GTT CTG ATT CCT ACG AAG GGC TTT GTG TCA GCC GTT AGT AAC ATG   823
195  V   P   R   N   V   L   I   P   T   K   G   F   V   S   A   V   S   N   M    214

824  CGC TCA TTT GTC CCA GCT ATC TAT GAC TTC AGG CTC ACA GTC GCC ATT CCT AAA ACC ACC GAA CAA   883
215  R   S   F   V   P   A   I   Y   D   F   R   L   T   V   A   I   P   K   T   T   E   Q    234

884  CCT ACA ATG CTC AGA CTC AGA CTC AGA GAC TTC CCT AAA ACA GAT CAC GTA CAC CTT AAG CGC   943
235  P   T   M   L   R   L   R   D   L   F   K   T   D   H   V   H   L   K   R    254

944  CAT TTG AAG GAC TTC CCT AAA ACA GAT CAC CAG GTT GCA CAG TGG TGT AAA GAT CAA   1003
255  H   L   K   D   L   F   K   T   D   H   Q   V   A   Q   W   C   K   D   Q    274

1004 TTT ATA TCC AAG GAT GCA TTG CGG CCA AGT AAG TCT CTT GTC GTC GAT GCT GAG GAT GGC CTG   1063
275  F   I   S   K   D   A   L   R   P   S   K   S   L   V   V   D   A   E   G   L    294

1064 GAA GTG CAG GAC ATT GGT TTG GGG CTT GTG AAA TTT CTT CGG GCA TCT GAG GAT ACT TTC AGT TGG TGC   1123
295  E   V   Q   D   I   G   L   G   L   V   K   F   L   R   A   S   E   D   T   F   S   W   C    314

1124 CTA CTC TGT ATG ATG ACG ACA TTC GTT CTG AAA TTT CTT ATG TGG TCA GCA CTT TTA TCC ATG TGG   1183
315  L   L   C   M   M   T   T   F   V   L   K   F   L   M   W   S   A   L   L   S   M   W    334

1184 GGT ATG ATG ATA ACG ACA TTC GTT CTG CTC GGA ATC GTG ACC CCG AAG ACG CTT ATC CAC ATG ATC TTG ATA   1243
335  G   M   M   I   T   T   F   V   L   L   G   I   V   T   P   K   T   L   I   H   M   I   L   I    354

1244 CGT TCT TCC CAG TCA GAG CAT TCA ACC CCG GCA AAG ACG AGG GCC AGA CAA ACT GCA GAG   1303
355  R   S   S   Q   S   E   H   S   T   P   A   K   T   R   A   R   Q   T   A   E    374

1304 AAC CCA AAA TGA AATAAGCTTTTTCTTATTAAGGAAGGTATATCAT ATG TAG TA ATG TGG GTT   1370
375  N   P   K   *                                      M   *      M   W   V    3

1371 TCC TTC ATT TAC CAA TGG ATT TAT GTT GTT ATC AAT GCG GAA GAA TTA AGA TGT TTT TTC   1430
4    S   F   I   Y   Q   W   I   Y   V   V   I   N   A   E   E   L   R   C   F   F   L    23

1431 CCT TCC GGA GTT GTT TTA CTC TAT AGA CTT GTA TGC TCA AT ATG CAC AAT TAG ACAT ATG   1490
24   P   S   G   V   V   L   L   Y   R   L   V   C   *      M   H   N   *      M    1

1491 TCA TTG TTT TAG CGGCCGCGAATTC                                                    1515
2    S   L   F   *                                                                   5
```

FIGURE 2

CLUSTAL V multiple sequence alignment

```
Lim 1 CB121  L  MAIPAAAFIVPISLLFFMSGLVVMFIQAVFYVLVRPISKDTYRRINTLVAELLWLELVWV
Maize        M  MAIPLVLVVLPLGLLFLLSGLJVNAJQQAVLFVTIRPFSKSFYRRINRFLAELLWLQLVWV
Rape         R  MAM-AAAVIVPLGILFFISGLVVNLLQ---------------------------------
                **. .*...**..***.**.*

L  IDWWAGVKVQLYTDTESFRLMGKFHALLICNHRSDIDWLIGWVLAQRCGCLSSIAVMKR
             M  VDWWAGVKVQLHADEETYRSMGKLHALTISNHRSDIDWLIGWILAQRSGCLGSTLAVMKF
             R  -------------------------------------RSGCLGSALAVMKK
                                                     * *** .*. *****

L  SSKFLPVIGWSHWFSEYLFLERNWAKDENTLKSGLQRLNDFPKPFWLAI.FVEGTRFTKAK
             M  SSKFLPVIGWSHWFAEYLFLERSWAKDEKTLKWGI.QRI.KDFPRPFWLALFVEGTREFTPAK
             R  SSKFLPVIGWSMWFSEYLFLERNWAKDESTLKSGLQRLNDFPRPFWLALFVEGTRFTEAK
                ************ *********.*****..***.*.*****.*********** **

L  LLAAQEYAASAGLPVPRNVLIPRTKGFVSAVSNMRSFVPAIYDLTVAIPKTTEQPTMLKL
             M  LLAAQEYAASQGLPAPRNVLIPRTKGFVSAVSIMRDFVPAIYDTTVIVPKDSPQPTMLRI
             R  LKAAQEYAASSELPVPRNVLIPRTKGFVSAVSNMRSFVPAIYDMTVAIPKTSPPPTMLRL
                * ********  ** ***************. **.*******.** .* .  **** .

L  FRGKSSVVHVHLKRHLMKDLPITDDGVAQWCKDQFISKDALLDKHVAEDTFSGLEVQDIG
             M  LKGQSSVIHVRMKRHAMSEMPKSDEDVSKWCKDIFVAKDALLEKHLATGIF-DEFIRPIG
             R  FKGQPSVVHVHIKCHSMKDLPESEDEIAQWCRDQFVTKDALLDKHIAADTFAGGKEQNIG
                . * **.** .* *.* ..   .**  .**.* *..***** **.*   .*   .  **

L  RPMKSLVVVSWMCLLCLGLVKFLQWSALLSSWKGMMITTFVLGIVTALMHILIRSSQSE
             M  RPVKSLLVTLFWSCLLLFGAIEFFKWTQLLSTWRGYAFTAAGMALVTGVMHVFIMFSQAE
             R  RPIKSLAVVLSWACLLTLGAMKFLHWSNLFSSWKGLALSALGLGITILCMQILIRSSQSE
                ** ***.*   *  **   *  *  *. * ** *     . .  .* .   .. **.*

L  HSTPAK--------------TRARQTAEMPK
             M  RSSSARAARNRYK---------------KEX
             R  RSTPAKVAPAKPKDNHQSGPSSQTEVEEKQK
                .*.*
```

```
*  Conserved between 3 sequences
.  Conserved between 2 sequences
```

FIGURE 3 correct pCB129 cDNA -> 1-phase Translation

DNA sequence   1075 b.p.   GTTCTATTCATG ... TCTTGAAAAAAA   linear

```
1/1                                              31/11
GTT CTA TTC ATG GCC AAA ACT AGA ACT AGC TCT CTC CGC AAC AGG AGA CAA CTA AAG CCG
 V   L   F   M   A   K   T   R   T   S   S   L   R   N   R   R   Q   L   K   P
61/21                                            91/31
GCT GTA GCT GCT ACT GCT GAT GAT GAT AAA GAT GGG GTT TTT ATG GTA TTG CTA TCG TGT
 A   V   A   A   T   A   D   D   D   K   D   G   V   F   M   V   L   L   S   C
121/41                                           151/51
TTC AAA ATT TTT GTT TGC TTT GCG GTA GTG TTG ATC ACG GCG GTC GCA TGG GGA CTA ATC
 F   K   I   F   V   C   F   A   V   V   L   I   T   A   V   A   W   G   L   I
181/61                                           211/71
ATG GTC CTG CTC TTA CCT TGG CCT TAT ATG AGG ATT CGA CTA GGA AAT CTT TAC GGC CAT
 M   V   L   L   L   P   W   P   Y   M   R   I   R   L   G   N   L   Y   G   H
241/81                                           271/91
ATC ATT GGT GCA TTA GTG ATA TGG ATT TAC GGA ATA CCA ATA AAG ATC CAA GGA TCC GAG
 I   I   G   G   L   V   I   W   I   Y   G   I   P   I   K   I   Q   G   S   E
301/101                                          331/111
CAT ACA AAG AAG AGG GCC ATT TAT ATA AGC AAT CAT GCT TCT CCT ATC GAT GCT TTC TTT
 H   T   K   K   R   A   I   Y   I   S   N   H   A   S   P   I   D   A   F   F
361/121                                          391/131
GTT ATG TGG TTG GCT CCC ATA GGC ACA GTT GGT GTT GCA AAG AAA GAG GTT ATA TGG TAT
 V   M   W   L   A   P   I   G   T   V   G   V   A   K   K   E   V   I   W   Y
421/141                                          451/151
CCG CTA CTT GGA CAA CTA TAT ACA TTA GCC CAT CAT ATT CGT ATA GAT CGG TCA AAC CCG
 P   L   L   G   Q   L   Y   T   L   A   H   H   I   R   I   D   R   S   N   P
481/161                                          511/171
GCT GCG GCT ATT CAG TCT ATG AAA GAG GCA GTT CGT GTA ATA ACC GAA AAG AAT CTC TCT
 A   A   A   I   Q   S   M   K   E   A   V   R   V   I   T   E   K   N   L   S
541/181                                          571/191
CTG ATT ATG TTT CCA GAG GGA ACC AGG TCG GGA GAT GGG CGT TTA CTT CCT TTC AAG AAG
 L   I   M   F   P   E   G   T   R   S   G   D   G   R   L   L   P   F   K   K
601/201                                          631/211
GGT TTT GTT CAT CTA GCA CTT CAG TCA CAC CTC CCG ATA GTT CCG ATG ATC CTT ACA GGT
 G   F   V   H   L   A   L   Q   S   H   L   P   I   V   P   M   I   L   T   G
661/221                                          691/231
ACA CAT TTA GCA TGG AGG AAA GGT ACC TTC CGT GTC CGG CCA GTA CCC ATC ACT GTC AAG
 T   H   L   A   W   R   K   G   T   F   R   V   R   P   V   P   I   T   V   K
721/241                                          751/251
TAC CTT CCT CCT ATA AAC ACT GAT GAT TGG ACT GTT GAC AAA ATC GAC GAT TAC GTC AAA
 Y   L   P   P   I   N   T   D   D   W   T   V   D   K   I   D   D   Y   V   K
781/261                                          811/271
ATG ATA CAC GAC ATC TAT GTC CGC AAC CTA CCT GCG TCT CAA AAA CCA CTT GGT AGC ACA
 M   I   H   D   I   Y   V   R   N   L   P   A   S   Q   K   P   L   G   S   T
841/281                                          871/291
AAT CGC TCA AAG TGA GTC GCT CTT TAC TCC AAG GTT AGC ATA ATG GAT ACG TAC TTT AGT
 N   R   S   K   *   V   A   L   Y   S   K   V   S   I   M   D   T   Y   F   S
901/301                                          931/311
CTT GCT GCA TGA AAA GTT TAA TCC TTT CTT GTG ATA TTA GAT TAC AGC GTA AGA CTT TCA
 L   A   A   *   K   V   *   S   F   L   V   I   L   D   Y   S   V   R   L   S
961/321                                          991/331
TGT TAA AGT AGT GTA ACA GTG CTT CTT GTT TCT AAC TTT TAC AAT AAA AGT ACC CTT TTG
 C   *   S   S   V   T   V   L   L   V   C   N   F   Y   N   K   S   T   L   L
1021/341                                         1051/351
AAG AAG GGA GCA AGG TTT AAA TAG AAA CGA GTT CTA GTT CTT CTC TTC AAA AAA A
 K   K   G   A   R   F   K   *   K   R   V   L   V   L   L   F   K   K
```

FIGURE 4

| | Init | Opt | tid | o'lap | | |
|---|---|---|---|---|---|---|
| 1 | 142 | 279 | 35.3 | 187 | PLSC_YEAST | POSSIBLE 1-ACYL-SN-GLYCEROL-3-PHOSPHATE ACYLTRANSFERASE (EC 2.3.1.51). - SACCHAROMYCES CEREVISIAE (BAKER'S YEAST). |
| 2 | 227 | 279 | 27.9 | 244 | PLSC_ECOLI | 1-ACYL-SN-GLYCEROL-3-PHOSPHATE ACYLTRANSFERASE (EC 2.3.1.51). - ESCHERICHIA COLI. |
| 3 | 225 | 273 | 27.5 | 244 | PLSC_SALTY | 1-ACYL-SN-GLYCEROL-3-PHOSPHATE ACYLTRANSFERASE (EC 2.3.1.51). - SALMONELLA TYPHIMURIUM. |
| 4 | 225 | 247 | 32.1 | 187 | B45582 | ParF=small hydrophobic protein - Salmonella typhimurium |
| 5 | 61 | 122 | 22.1 | 195 | AAS_ECOLI | 2-ACYLGLYCEROPHOSPHOETHANOLAMINE ACYLTRANSFERASE/ACYL-ACYL CARRIER PROTEIN SYNTHETASE. - ESCHERICHIA COLI. |
| 6 | 56 | 113 | 28.6 | 56 | VE5_HPV33 | PROBABLE E5 PROTEIN. - HUMAN PAPILLOMAVIRUS TYPE 33. |
| 7 | 62 | 100 | 25.3 | 87 | NU5M_DROYA | NADH-UBIQUINONE OXIDOREDUCTASE CHAIN 5 (EC 1.6.5.3). - DROSOPHILA YAKUBI (FRUIT FLY). |
| 8 | 80 | 100 | 28.6 | 56 | VE5_HPV58 | PROBABLE E5 PROTEIN. - HUMAN PAPILLOMAVIRUS TYPE 58. |
| 9 | 61 | 96 | 20.9 | 134 | YSCH817913 | YSCH8179 NCBI gi: 488176 - Saccharomyces cerevisiae |
| 10 | 53 | 96 | 17.1 | 205 | A45264 | IBAT=71.8 kDa protein related to b0,+ amino acid transporter system for dibasic and neutral amino acids - rabbit |
| 11 | 53 | 96 | 17.1 | 205 | A45048 | rBAT-2=amino acid transport protein - rabbit |
| 12 | 56 | 94 | 18.5 | 108 | HSMALB | HSMALB NCBI gi: 435480 - Homo sapiens |
| 13 | 55 | 93 | 16.0 | 156 | JS0734 | endo-1,4-beta-xylanase (EC 3.2.1.8) precursor - fungus (Pilobasidium floriforme) |
| 14 | 80 | 93 | 19.7 | 71 | DESA_SYNY3 | FATTY ACID DESATURASE (EC 1.14.99.--). - SYNECHOCYSTIS SP. (STRAIN PCC 6803). |
| 15 | 54 | 91 | 18.0 | 122 | HPCFPA | HPCFPA NCBI gi: 469211 - Hepatitis C virus |
| 16 | 82 | 91 | 21.1 | 71 | SYCDESA | SYCDESA NCBI gi: 488509 - Synechocystis sp. |
| 17 | 76 | 90 | 26.9 | 78 | QAY_NEUCR | QUINATE TRANSPORTER. - NEUROSPORA CRASSA. |
| 18 | 65 | 86 | 27.3 | 66 | OUTO_ERWCH | TYPE 4 PREPILIN-LIKE PROTEIN SPECIFIC LEADER PEPTIDASE (EC 3.4.99.--). (PECTIC ENZYMES SECRETION PROTEIN OUTO). - ERWINIA CHRYSANTHEMI. |
| 19 | 61 | 85 | 34.1 | 44 | YORR_TTV1 | HYPOTHETICAL 7.4 KD PROTEIN. - THERMOPROTEUS TENAX VIRUS 1 (STRAIN KRA) (TTV1). |
| 20 | 75 | 85 | 19.2 | 52 | STODESA2 | STODESA2 NCBI gi: 488511 - Synechococcus sp. |
| 21 | 72 | 84 | 31.0 | 42 | YIJE_ECOLI | HYPOTHETICAL 34.1 KD PROTEIN IN KATG-GLDA INTERGENIC REGION (OJ2). - ESCHERICHIA COLI. |
| 22 | 56 | 84 | 20.0 | 75 | MAL_HUMAN | T-LYMPHOCYTE MATURATION-ASSOCIATED PROTEIN. - HOMO SAPIENS (HUMAN). |
| 23 | 69 | 83 | 22.5 | 80 | JQ1724 | E1 membrane glycoprotein precursor - canine coronavirus (strain insavc-1) |
| 24 | 53 | 83 | 29.4 | 51 | YGL1_YEAST | HYPOTHETICAL MEMBRANE PROTEIN IN LEU1-SCL1 INTERGENIC REGION. - SACCHAROMYCES CEREVISIAE (BAKER'S YEAST). |

FIGURE 5

BESTFIT alignment of E. coli 2AT (PLSC) - top line and Limnanthes pCB129 protein bottom line.

```
         Gap Weight:     3.000        Average Match:   0.540
      Length Weight:     0.100        Average Mismatch: -0.396

Quality:    138.7                Length:    250
             Ratio:    0.573                  Gaps:      4
Percent Similarity:   50.207    Percent Identity:   26.971 c..a  x  k..a                      November 14, 1994  10:05

E coli      1 MLYIFRLIITVIYSILV...CVFGSIYCLFSPRNPKHVATFGHMFGRLAP  47
              |:..  : | |.: :::             .:|  |.|.|.  :: :|:::::|::
Lim 2 CB129  32 MVLLSCFKIFVCFAVVLITAVAWGLIMVLLLPWPYTMRI.RLGNLYGHIIG  80

48 ...LFGLKVECRKPTDAESYGNAIYIANHOMNIDMVTASNIVOPPIVTVG  94
               :: . : .::. .:::.   |||||.||..|. :. .:|..||.|:
           81 GLVIWIYGIPIKIQGSEBTKKRAIYISNHASPIDAPFVMHLAPIGTVGVA 130

95 KKSLLWIPFFGQLYWLTGNLLIDRNNRTKAHGTIAEVVNHPKKRRISIWM 144
              ||.::|.|:||||| | :.||||:  ||:.|.:. .:|.|.  .:|::
          131 KKEVIWYPLLGQLYTLAHHIRIDRSNPAAAIQSMKEAVRVITEENLSLIM 180

145 FPEGTRSRGRGLLPPKTGAFHAAIAAGVPIIPVCVSTT..SNKINLNRLH 192
              ||||||| * ||||||.|.|:.|.||.:|||||.||:.|||||||.||.|
          181 FPEGTRSGDGRLLPFKKGFVHLALQSHLPIVPMHILTGTBLAWRKGTFRVR 230

193 NGLVIVEMLPPIDVSQYGKDVQTVRELAAHCRSIMEQKIAELDKEVAEREAA 242
              . :.|. |||| |:... |:  .:: :  . . .|:|.::
          231 PVPITVKILPPINTDOWTVDKIDDYVXMIBDIIVRBLPASOKPLGSTNRS 280
```

FIGURE 6

BESTFIT alignment of part of Limnantes pCB129 protein with E. coli2-AT (PLSC)

```
       Gap Weight:    3.000      Average Match:    0.540
    Length Weight:    0.100      Average Mismatch: -0.396

Quality:   97.3              Length:  141
           Ratio:   0.700               Gaps:    1
Percent Similarity: 54.676    Percent Identity: 38.129 c.a x kdl.a                     December 1, 1994  11:39  ..

E coli  67 AIYIANHQNNYDMVTASNIVQPPTVTVGKKSLLWIPFFGQLYWLTGNLLI 116
           |||·||··|··|·  ·|·  ·||·|·||:||·:·|·|·|||| |·  :·|
Lim      2 AIYISNHASPIDAFFVMWLAPIGTVGVAKKEVIWTPLLGQLYTLAHHIRI 51

117 DRNNRTKABGTIAEVVNHFKKRRISIWMFPEGTRSRGRGLLPFKTGAFHA 166
           ||·|·|  ·|·|·|·  ·:|·|· ·:|: |||||||  |||||·|· ·|
Lim     52 DRSNPAAAIQSMKEAVRVITEENLSLIMFPEGTRSGDGRLLPFKKGFVHL 101

167 AIAAGVPIIPVCVSTT..SNKINLNRLHNGLVIVEMLPPID 205
           |:· ·||:|:·:·|·|   |:·  ·:·|··:·|· ||||·|
Lim    102 ALQSHLPIVPMILTGTHLAWRKGTFRVRPVPITVKLPPIN 142
```

FIGURE 7

Limnanthes (pCB129)=K versus E. coli 7-AT (PlsC)=C

CLUSTAL V multiple sequence alignment

```
C   MLY-------------------IFRLLITVIYSILVC------VFGSIYC
K   MAKTRTSSLRNRRQLKPAVAATADDDKDGVF-MVLLSCFKIFVCFAVVLITAVAWGLIMV
    *           .  .. .    *..**

C   LFSPRNFKHV----ATFGHMFGKLAP-LFGLKVFGRKPTDAESYGNAIYIANHQNNYDMVT
K   LLLPWPYMRIRLGNLYGHIIGGLVIWIYGIPIKIQGSEHTKK--RAIYISNHASPJDAFF
    **. **   .*..*      * .*  .*    * .

C   ASNIVQPPTVTVGKKSLLWIPFFGQLYWLTCNLLIDRNNRTKAHGTIAEVVNHFKKRRIS
K   VMWLAPIGTVGVAKKFVIWYPLLGQLYTLAHHIRIDRSMPAAAIQSMKEAVRVITEFNLS
    ** *   . . *** * *   *.**    ****.

C   IWMPPFGTRSRGRGLLPFKTGAFHAAIAAGVPIIPVCVSTT--SNKINLNRLHNGLVIVE
K   LIMEPEGTRSGDGRLLPFKKGFVHLALOSHLPIVPMILTGTHLAWRKGTFRVPPVPITVK
    * * * **** *  ****** *. *  .      .* .  .. .   *   . . . *

C   MLPPIDVSQYGKDQVRELAAHCRSIMEQKIAELDKEVARREAAGKY
K   YLPPINTDDWTVDKIDDYVKMIBDIYVRNLPASQKFLGSTNRSK--
    **** .                     *
``` coli
Lim 2 CB129

DNA SEQUENCE ENCODING PLANT 2-ACYLTRANSFERASE

This application is a continuation of PCT International Application No. PCT/GB96/00306, filed Feb. 9, 1996, claiming priority of British Patent Application No. 9502468.3, filed Feb. 9, 1995.

This invention relates to modified plants. In particular, the invention relates to plants modified such that at least part of the plant (for example seeds of the plant) is capable of yielding a commercially useful oil.

Plants have long been a commercially valuable source of oil. Nutritional uses of plant-derived oils have hitherto been dominant, but attention is now turning additionally to plants as a source of industrially useful oils, for example as replacements for or improvements on mineral oils. Oil seeds, such as from rape, have a variety of lipids in them (Hildish & Williams, "Chemical Composition of Natural Lipids", Chapman Hall, London, 1964). There is considerable interest in altering lipid composition by the use of recombinant DNA technology (e.g. Knauf, *TIBtech*, February 1987, 40–47), but by no means all of the goals have been realised to date for a variety of reasons, in spite of the ever-increasing sophistication of the technology.

Success in tailoring the lipid content of plant-derived oils requires a firm understanding of the biochemistry and genes involved. Broadly, two approaches are available. First, plants may be modified to permit the synthesis of fatty acids which are new (for the plant); so, for example, laurate and/or stearate may be synthesised in rape. Secondly, the pattern and/or extent of incorporation of fatty acids into the glycerol backbone of the lipid may be altered. It is with this latter approach that the present invention is concerned.

Lipids are formed in plants by the addition of fatty acid moieties onto the glycerol backbone by a series of acyl transferase enzymes. There are three positions on the glycerol molecule at which fatty acid (acyl) moieties may be substituted, and the substitution reached at each position is catalysed by a position-specific enzyme; the enzymes are glycerol-sn-3-phosphate acyltransferase (1-acyltransferase), 1-acyl-sn-glycerol-3-phosphate acyltransferase (2-acyltransferase) and sn-1,2-diacylglycerol acyltransferase (3-acyltransferase).

One, but not the only, current aim of "lipid engineering" in plants is to provide oils including lipids with a higher content of erucic (22:1) acid and/or oils containing trierucin. Erucic acid-containing lipids are commercially desirable for a number of purposes, particularly as replacements to or supplements for mineral oils in certain circumstances, as alluded to above. In the case of oil seed rape (*Brassica napus*), one of the most significant oil producing crops in cultivation today, the specificity of the 2-acyltransferase enzyme positively discriminates against the incorporation of erucic acid at position 2. So, even in those cultivars of rape which are able to incorporate erucic acid at positions 1 and 3, where there is no (or at least reduced) discrimination against erucic acid, only a maximum 66% of the fatty acids incorporated into triacyl glycerols can be erucic acid. Such varieties of rape are known as HEAR (high erucic acid rape) varieties.

It would therefore be desirable to produce plants, eg conventional oil seed rape as well as HEAR varieties, which contain useful levels of trierucin and/or contain higher levels of erucic acid and/or contain oils with erucic acid incorporated at position 2; the same can be said of oils of other vegetable oil crops such as maize, sunflower and soya, to name but a few examples. While in principle it may be thought possible to introduce into a desired plant DNA encoding a 2-acyltransferase of different fatty acid specificity, for example from a different plant, in practice there are a number of problems.

All enzymes involved in the acylation pathway for formation of triacylglycerols are membrane bound. These are the 1-acyltransferase, 2-acyltransferase and 3-acyltransferase which are present in the endoplasmic reticulum in the cytoplasm. They have not been purified. This makes working with them difficult and rules out the use of many conventional DNA cloning procedures. This difficulty does not, paradoxically, lie in the way of cloning the gene (or at least cDNA) encoding the Choroplastic 1-acyltransferase enzyme, which is soluble; in fact, recombinant DNA work has already been undertaken on this enzyme for a completely different purpose, namely the enhancement of chilling resistance in tobacco plant leaves, by Murata et al (*Nature* 356 710–713 (1992)).

Wolter et al, Fat Science Technology, 93, No 8: 288–89 (1991) suggested a strategy for cloning membrane bound enzymes such as 2-acyltransferases, although no exemplification was given.

WO-A-9413814 discloses a DNA sequence (and corresponding protein sequence) of a 2-acyltransferase. This sequence, which is derived from maize, is used to transform plants, such that the normal substrate specificity of the plants' 2-acyltransferase is altered. This disclosure also included the use of a cDNA sequence for a 2-AT derived from maize to locate 2-ATs with a high degree of homology from both Brassica and Limnanthes species.

It has now been surprisingly found that there is in fact another 2-AT in Limnanthes which has no homologue in rape and which is seed specific. This 2-AT is able to incorporate erucic acid at the 2-position which the native 2-AT in rape, for example, is unable to do.

According to a first aspect of the invention, therefore, there is provided a recombinant or isolated DNA sequence, encoding an enzyme having membrane-bound 2-acyltransferase activity, and selected from:
(i) a DNA sequence comprising the DNA sequence of FIG. 3 (SEQ ID NO: 7) or its complementary strand,
(ii) nucleic acid sequences hybridising to the DNA sequence of FIG. 3 (SEQ ID NO: 7) or its complementary strand, under stringent conditions, and
(iii) nucleic acid sequences which would hybridise to the DNA sequence of FIG. 3 (SEQ ID NO: 7) or its complementary strand, but for the degeneracy of the genetic code.

Suitably, the DNA sequence of the invention comprises a DNA sequence as described in (i), (ii) or (iii) above which is the sequence of FIG. 3, or its complementary strand, or is one which has the characteristics of (ii) or (iii) where the sequence is the sequence of FIG. 3 (SEQ ID NO: 7)

Fragments of the above DNA sequences, for example of at least 15, 20, 30, 40 or 60 nucleotides in length, are also within the scope of the invention.

Suitable stringent conditions include salt solutions of approximately 0.9 molar at temperatures of from 35° C. to 65° C. More particularly, stringent hybridisation conditions include 6 x SSC, 5 x Denhardt's solution, 0.5% SDS, 0.5% tetrasodium pyrophosphate and 50 μg/ml denatured herring sperm DNA; washing may be for 2×30 minutes at 65° C. in 1 x SSC, 0.1% SDS and 1×30 minutes in 0.2 x SSC, 0.1% SDS at 65° C.

Recombinant DNA in accordance with the invention may be in the form of a vector, which may have sufficient regulatory sequences (such as a promoter) to direct gene expression. Vectors which are not expression vectors are useful for cloning purposes (as expression vectors themselves may be). Host cells (such as bacteria and plant cells) containing vectors in accordance with the invention themselves form part of the invention.

The 2-acyltransferase of the invention may be cloned directly, for example using complementation studies, from a DNA library of Limnanthes. For example, if *E. coli* is used as the complementation host, a mutant is chosen which is defective in the 2-acyltransferase; the DNA library from Limnanthes (e.g. *L. douglasii*) is transformed into the mutant complementation host; host cells containing the target acyltransferase gene can readily be selected using appropriate selective media and growth conditions. *E. coli* mutant JC201 is a suitable host for use in complementation studies relating to 2-acyltransferase.

Cloning the acyltransferase gene into a microbial host, such as a bacterium like *E. coli,* in such a way that the gene can be expressed has a particular advantage in that the substrate specificity of the acyltransferase gene can be assessed with membranes isolated from the microbial host before transformed plants are prepared, thereby saving considerably on research time. Such an assessment may be made by competitive substrate assays, in which differently detectably labelled candidate substrates for the enzyme compete with each other for incorporation into the glyceride. For example, $^{14}$C-erucyl CoA and $^3$H-oleoyl CoA can be used as competitive substrates for 2-acyltransferase, and the relative amounts of $^{14}$C or tritium uptake into glyceride can be measured. (As 2-acyltransferases have acceptor, glycerol-based, substrates and donor, fatty acid-based, substrates, the experiment can be carried out with different acceptors, such as 1-erucyl-glycerol-3-phosphate and 1-oleoyl-glycerol-3-phosphate.) A gene coding for an enzyme which donates erucic acid to the acceptor (particularly 1-erucyl-glycerol-3-phosphate) may by this means be identified as a DNA sequence of choice for further use in the invention as described below.

Suitably, the DNA sequence of the invention encodes an enzyme having membrane-bound 2-acyltransferase activity.

The DNA sequence of the invention can be used to produce proteins which they encode, if desired. Thus, in a second aspect, the present invention provides an isolated protein which is the expression product of a DNA sequence of the invention. The protein may be expressed by host cells harbouring DNA in the form of an expression vector. The protein, an enzyme having 2-acyltransferase activity, may have an amino acid sequence which is identical to or homologous with the sequence shown in FIG. 3 (SEQ ID NO: 4). The degree of homology will generally be greater than that of known proteins, and may be at least 40, 50, 60, 70, 80, 90, 95 or 99%. Suitably, the degree of homology will be 60% or greater, preferably 80% or greater and most preferably 90% or greater.

In a third aspect, the present invention provides an antibody capable of specifically binding to a protein of the invention.

In a fourth aspect of the invention, there is provided a plant having a 2-acyltransferase enzyme encoded by a DNA sequence as defined herein, wherein the enzyme is not a native enzyme of the plant.

While site-directed mutagenesis and/or other protein engineering techniques may be used to alter the specificity of an enzyme native to the plant, it is preferred that the plant be transgenic and incorporate an expressible 2-acyltransferase gene encoding the enzyme of the invention. For example, as described above, the 2-acyltransferase enzyme which does not discriminate against erucic acid, may be made by this means to express in a plant which would not normally incorporate erucic acid at the 2-position into triacylglycerides. An important embodiment of the invention relates to genetically engineered plants which contain trierucin. Such plants may thus also have higher levels of erucic acid incorporated into triacylglycerols than in corresponding non-engineered plants(eg. rape).

However, while a preferred approach is discussed above, the invention includes modified 2-acyltransferase proteins obtained by methods well known in the art. The essential feature that such proteins should possess is, of course, the specificity for incorporating erucic acid at position 2 of TAGs. However, using a variety of techniques modified enzymes can be obtained which have, for example, greater heat stability, improved kinetic characteristics or even improved specificity for erucic acid.

Suitable examples of such engineered plants include Brassica eg *B. napus, B. campestris,* B. Juncea or *B. rapa,* maize, sunflower or soya.

For the 2-acyltransferase transgene to be expressible, a promoter has to be operatively coupled to it. Because at the present state of the art it is difficult precisely to regulate the site of incorporation of a transgene into the host genome, it is preferred that the transgene be coupled to its promoter prior to transformation of the plant. Promoters useful in the invention may be temporal- and/or seed-specific, but there is no need for them to be so: constitutive promoters may also be used provided they are suitably strongly expressed in the seed and are easier to isolate. Other tissues are unlikely to be adversely affected if the transgene encoding the acyltransferase enzyme is expressed in them, as the availability of the fatty acid CoA substrates is effectively limited to the seed.

The promoter-transgene construct, once prepared, is introduced into plant cells by any suitable means. The invention extends to such plant cells. Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

The plants of the invention include ones which therefore have higher levels of erucic acid incorporated at the 2-position of their triacylglycerols (TAGs) as well as plants which contain trierucin.

Preferably DNA in accordance with the invention also contains a second chimeric gene (a "marker" gene) that enables a transformed plant or tissue culture containing the foreign DNA to be easily distinguished from other plants or tissue culture that do not contain the foreign DNA. Examples of such a marker gene include antibiotic resistance (Herrera-Estrella et al, *EMBO J*. 2(6) 987–95 (1983) and Herrera-Estrella et al, *Nature* 303 209–13 (1983)), herbicide resistance (EP-A-0242246) and glucuronidase (GUS) expression (EP-A-0344029). Expression of the marker gene is preferably controlled by a second promoter which allows expression in cells in culture, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

In one embodiment of the invention, the transgenic plant's native 2-acyltransferase gene which corresponds to the transgene may be rendered at least partially inoperative or reduced in effectiveness by, for example, antisense or ribozyme techniques, as is known in the art.

A whole plant can be regenerated from a single transformed plant cell; and the invention therefore provides transgenic plants (or parts of them, such as propagating material) including DNA in accordance with the invention as described above. The regeneration can proceed by known methods.

Therefore, in a fifth aspect, the present invention provides a plant cell incorporating a DNA sequence of the invention.

In a sixth aspect, the invention provides seeds obtained from a plant of the invention.

By means of the invention, plants generating oil with a tailored lipid content may be produced. For example, plants which produce trierucin and/or incorporate erucic acid at position 2 of triacylglycerols (TAGs) can be engineered. In addition, the lipid composition of triacylglycerides in the plant may be substantially altered to produce triacylglycerides with a desired erucic acid content higher than has hitherto been possible. For example, oil seed rape (*B. napus*) may be transformed to produce oil whose triacylglyceride has an erucic acid content which is higher than that obtained in untransformed plants. Similarly for other oil producing crops.

Promoters which naturally drive 2-acyltransferases may also be obtained by hybridisation and/or restriction enzyme analysis and/or sequencing studies using the FIG. 3 (SEQ ID NO: 7) sequence.

In further aspects, the present invention provides:

(a) a method of generating oil, the method comprising cultivating a plant of the invention and harvesting oil produced by the plant or a part (particularly seeds) thereof;

(b) oil obtained from a plant of the invention, or a part thereof, or from seeds of the invention which has erucic acid incorporated at the 2-position of its TAGs;

(c) oil obtained from a plant of the invention, or a part thereof, or from seeds of the invention which contains trierucin;

(d) a microbial host transformed with a DNA sequence of the invention;

(e) an oil seed rape plant, or other oil producing crop plant, containing trierucin;

(f) an oil seed rape plant, or other oil producing crop plant, having erucic acid incorporated at the 2-position of its TAGs; and (g) a transgenic plant which expresses in at least some of its cells a DNA sequence of the invention. In particular, the DNA sequence is expressed in the seeds of the plant.

Preferred features of each aspect of the invention are as for each other aspect mutatis mutandis.

The invention is illustrated by the following examples. The examples refer to the accompanying drawings, in which:

FIG. 1: shows the cDNA sequence (SEQ ID NO: 3) derived in Example 2 and its derived protein sequence (SEQ ID NO: 4).

FIG. 2: shows a comparison of the sequences of rape (SEQ ID NO: 6), maize (SEQ ID NO: 5) and the Limnanthes '1' (SEQ ID NO: 4) clone.

FIG. 3: shows the cDNA sequence of pCB129 (SEQ ID NO: 7) described in Example 3.

Figure 9A:
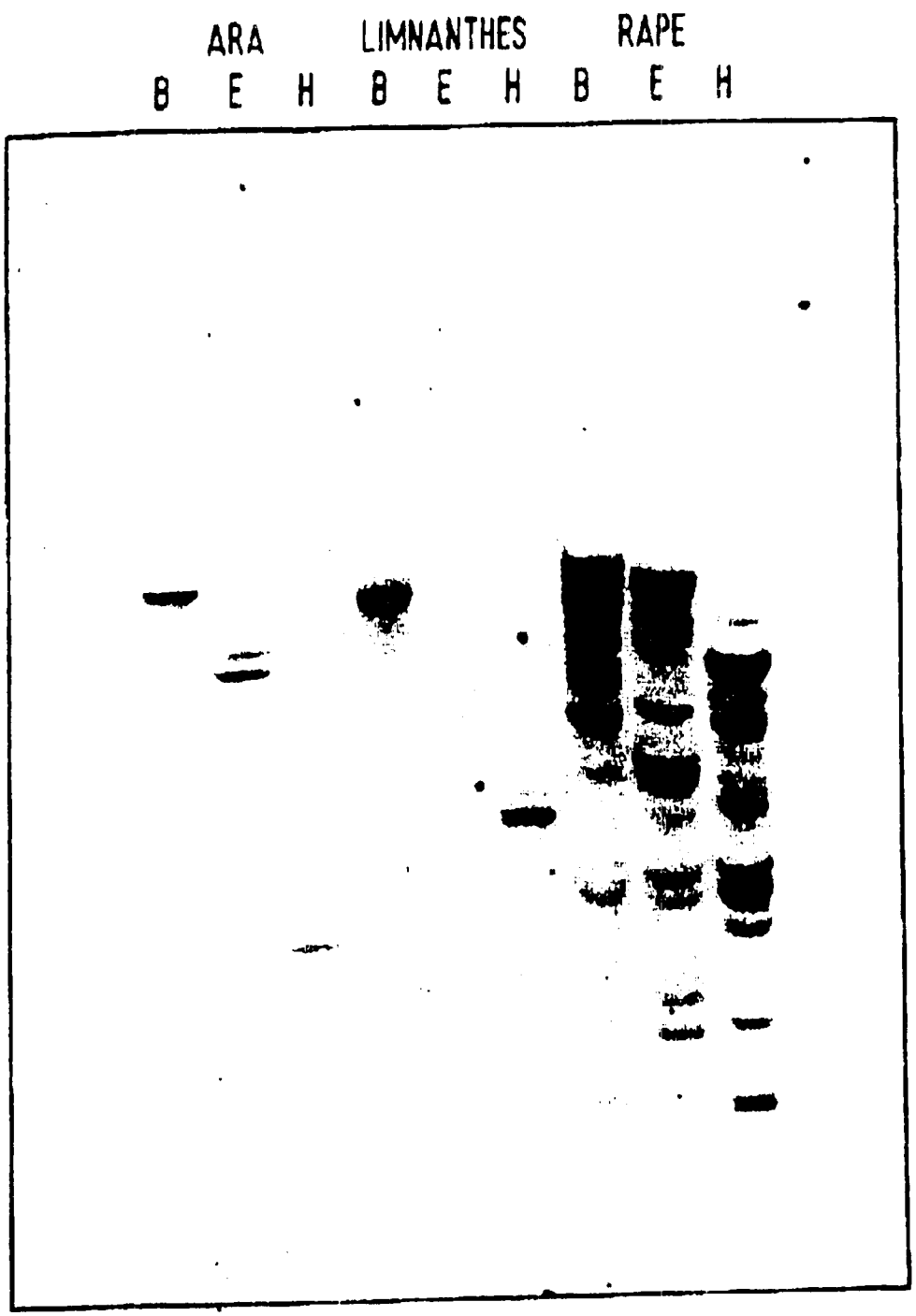
Figure 9B:
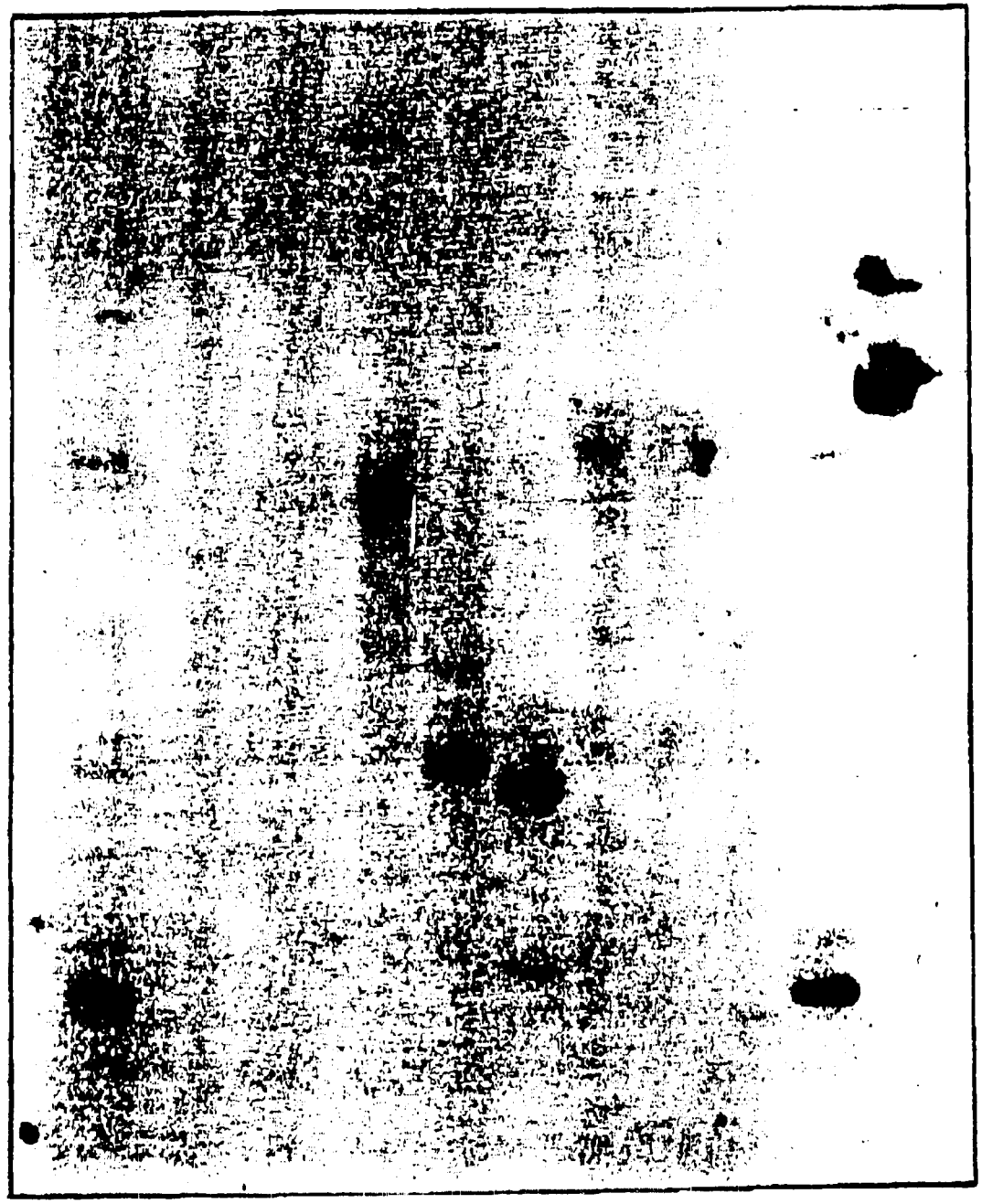
Figure 9C:
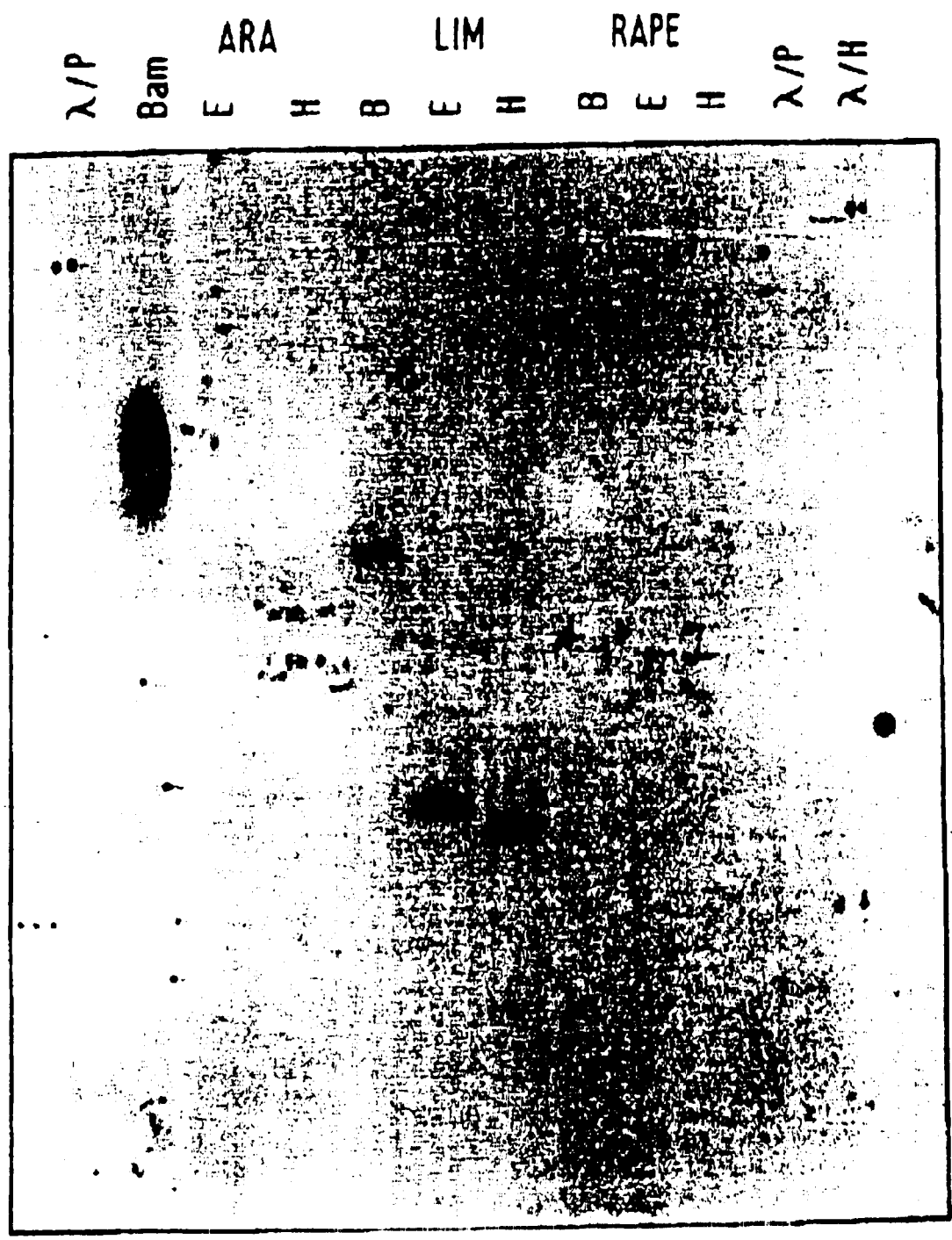

FIG. 4: shows the results of a homology search using the sequence of FIG. 3 against the OWL database;

FIGS. 5 and 6: show BESTFIT alignment of the sequence of FIG. 3 (SEQ ID NO: 7) compared with the sequence of *E. coli* 2-AT (FIG. 5 (SEQ ID NO: 9 and SEQ ID NO: 10)); as well as bestfit alignment of part of the Limnanthes sequence from FIG. 3 with *E. coli* 2-AT (FIG. 6 (SEQ ID NO: 11 and SEQ ID NO: 12)). Lines indicate exact matches between the aligned sequences. Double points indicate conservative amino acid substitutions, and single points, pairs of amino acids conserved to a lesser degree;

FIG. 7 (SEQ ID NO: 8 and SEQ ID NO: 13): shows an alignment of the sequence of FIG. 3 with the top-matching sequence from *E. coli* 2-AT;

FIG. 8: shows the results of Northern Blot analysis of RNA from Limnanthes embryo, leaf and stem probed with a fragment of the Limnanthes 2 (CB129);

FIGS. 9*a–c*: show the results of the Southern blot analysis described in Example 6.

Figure 10:
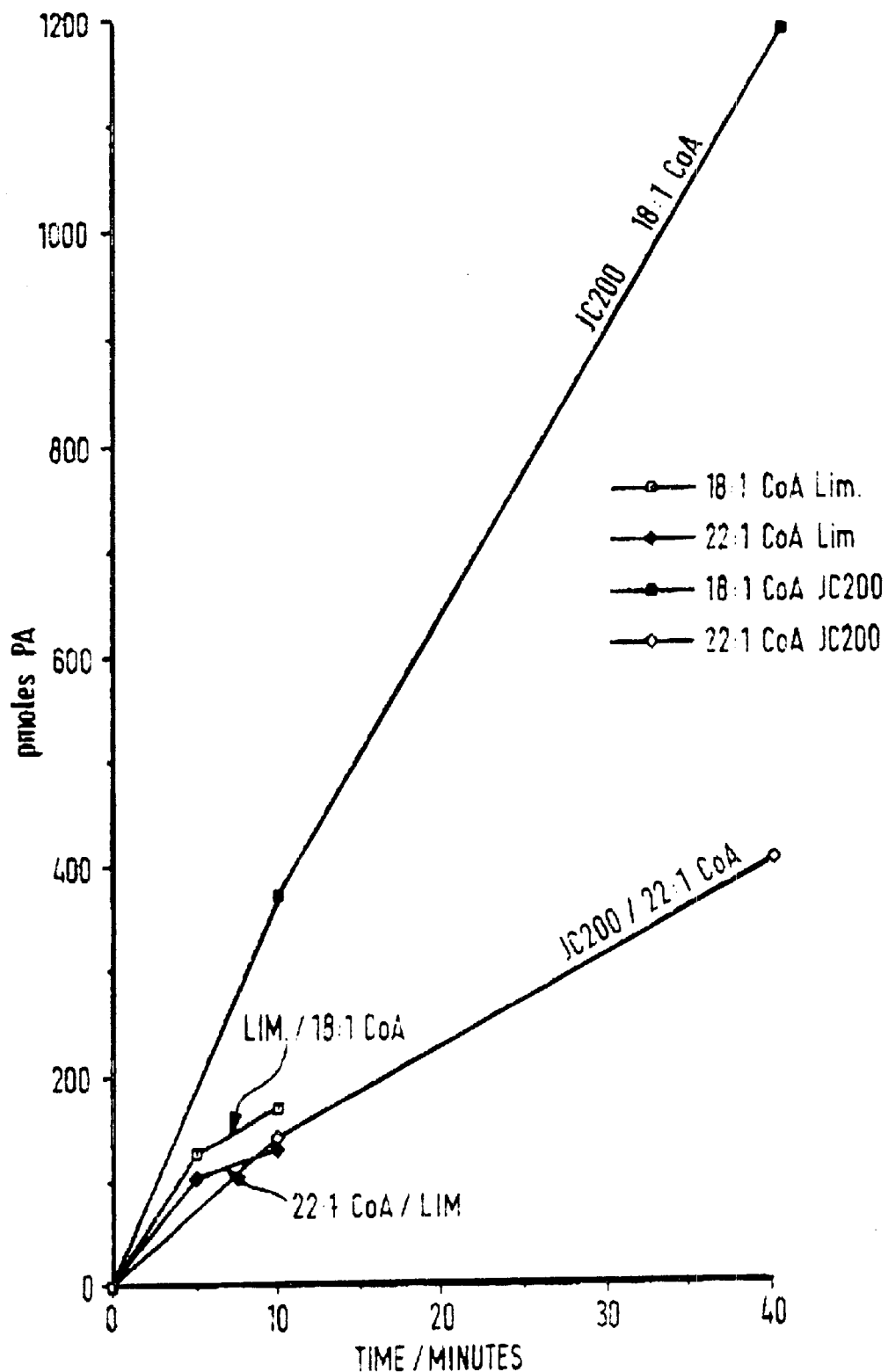
Figure 11:
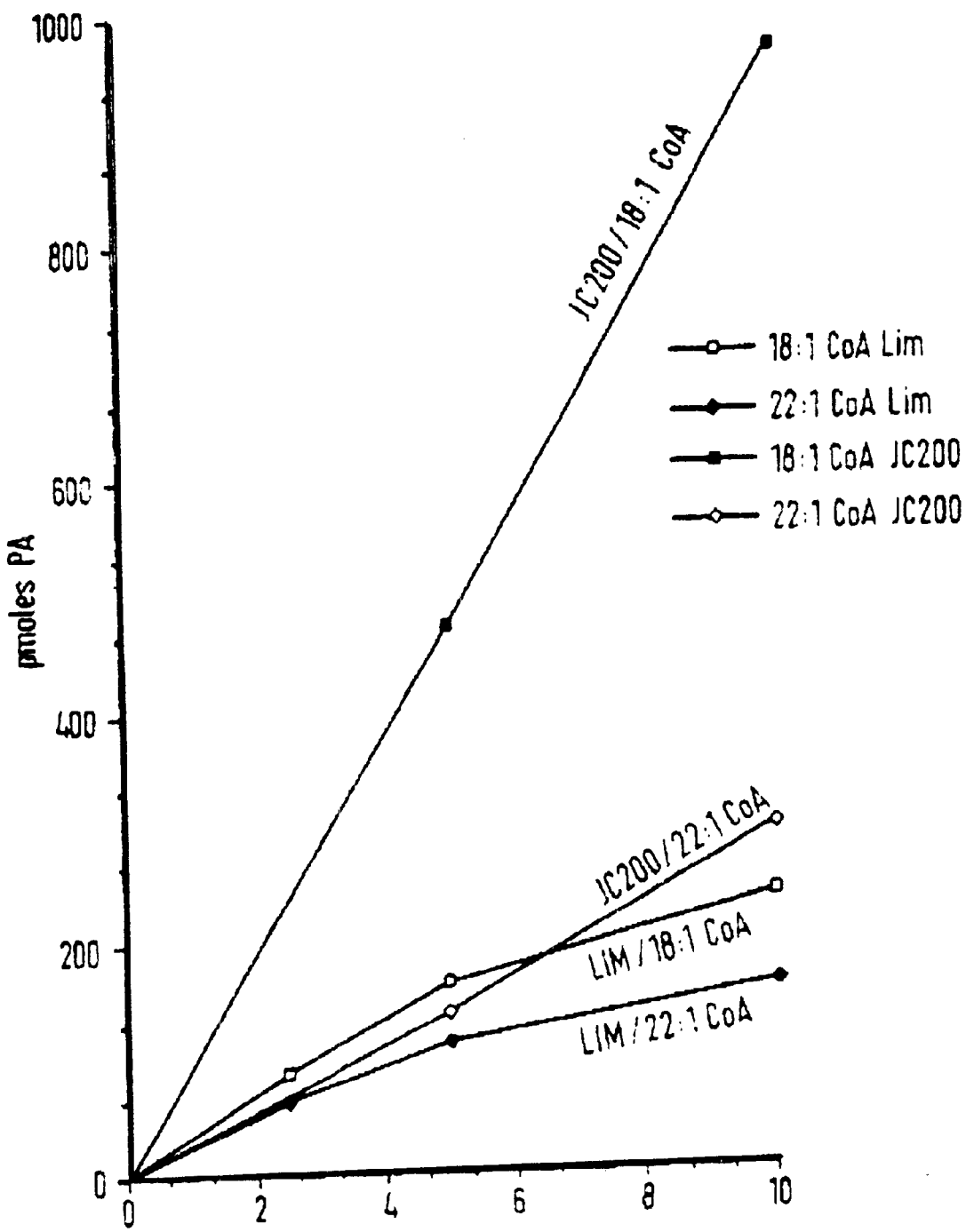
Figure 12:
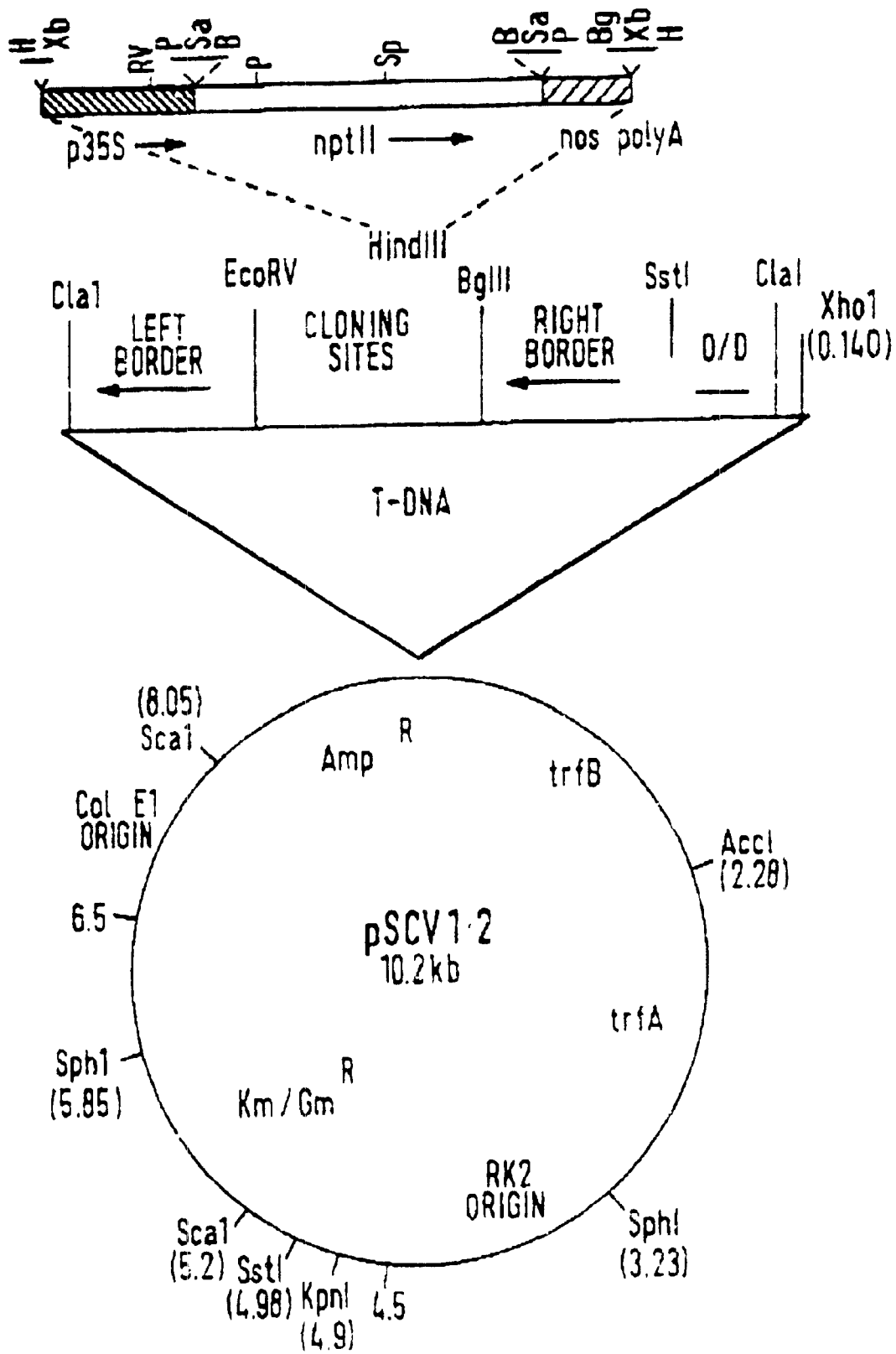
Figure 13:
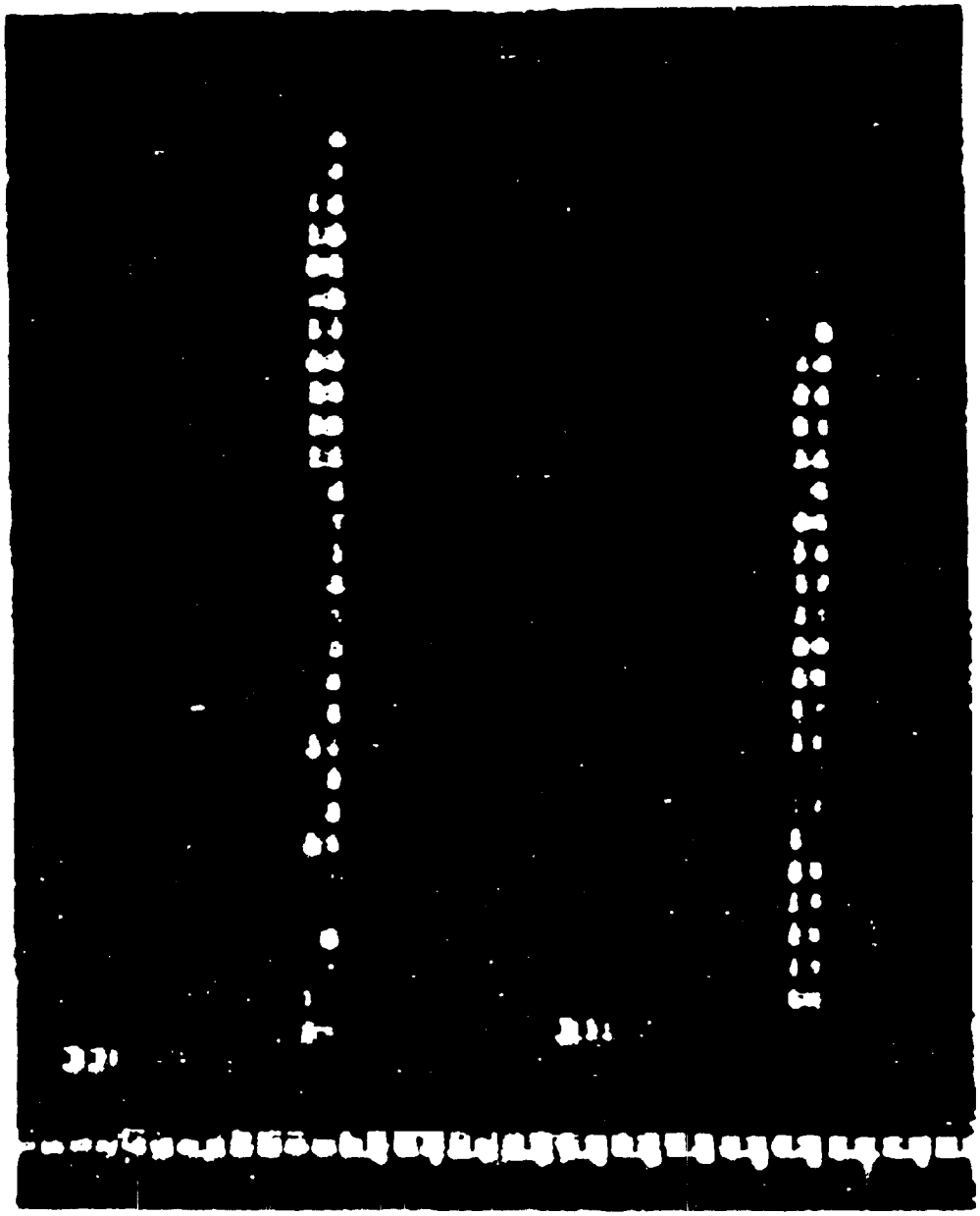
Figure 14A:
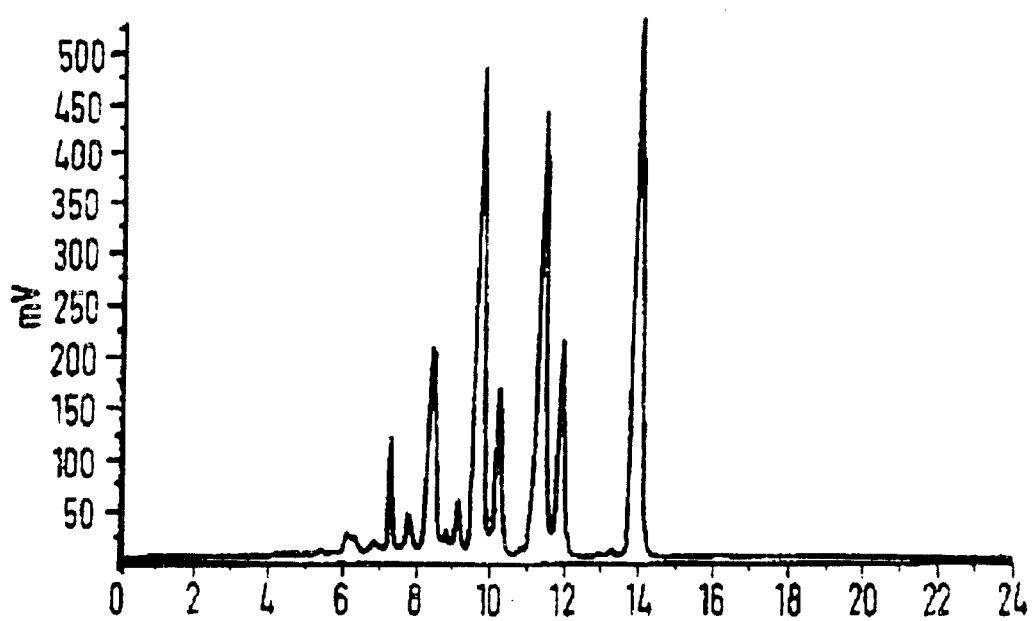
Figure 14B:
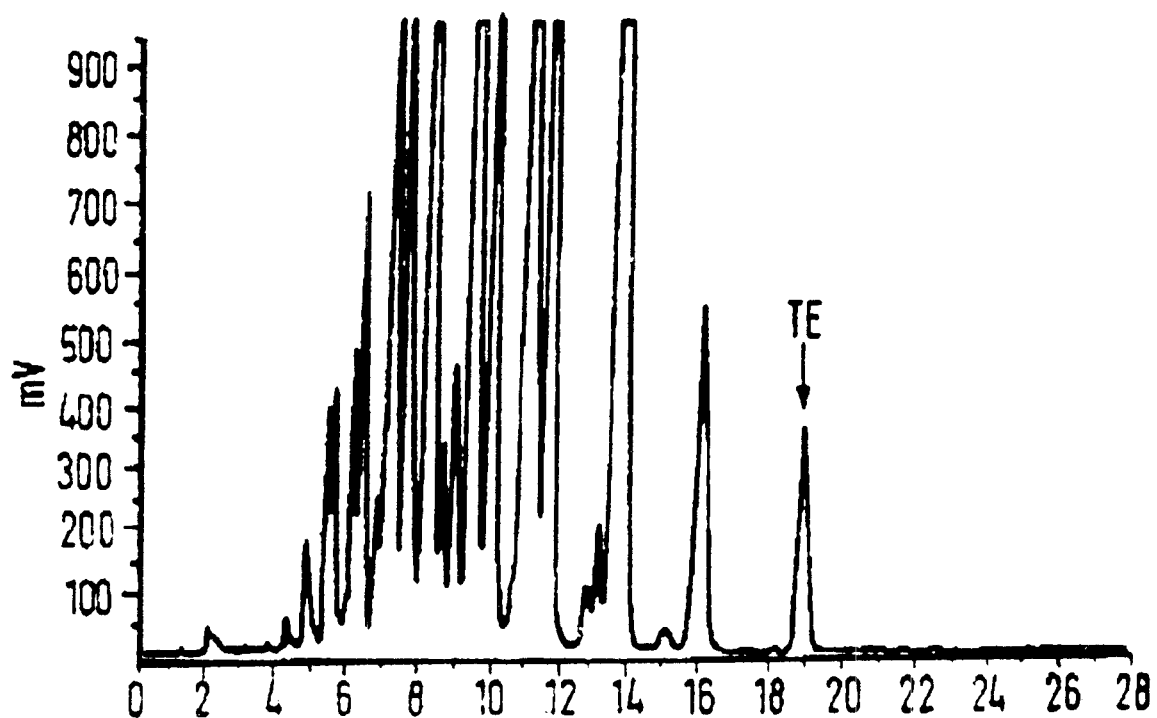
Figure 14C:
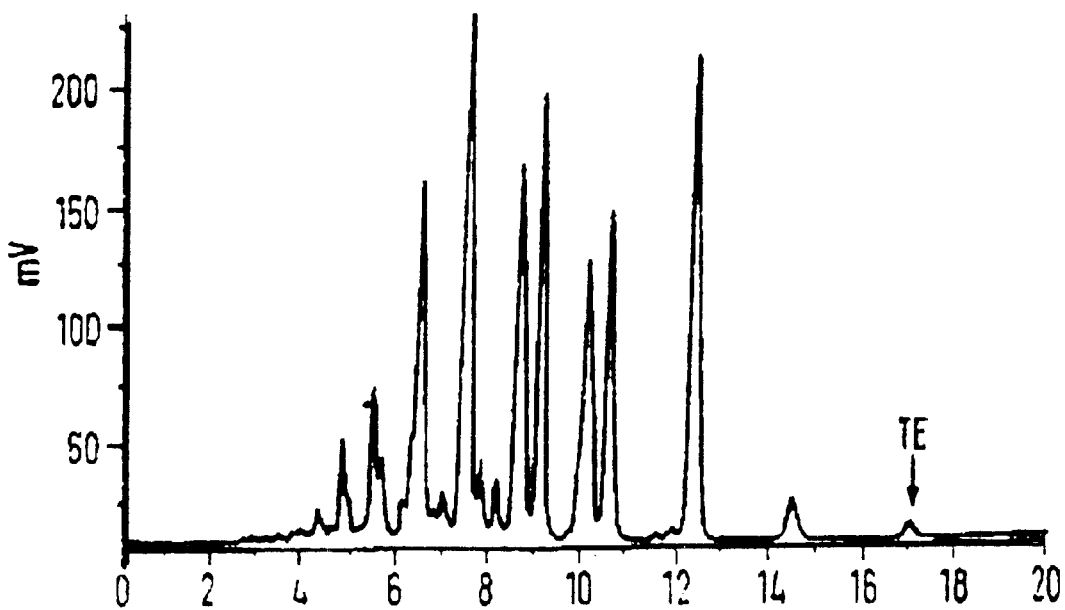

FIG. 10: shows the results of substrate specificity assays using membranes from JC201 (containing pCB129) and JC200;

FIG. 11: shows the results of further substrate specificity assays using membranes from JC201 (containing pCB129) and JC200;

FIG. 12: is a map of plasmid pSCV1.2 referred to in Example 8;

FIG. 13: shows the results of the PCR procedure carried out in Example 9;

FIG. 14: shows reverse-phase HPLC analysis of seed triacylglycerols; and

FIG. 15: shows mass spectral assignment of trierucin.

EXAMPLE 1

Construction of library

*Limnanthes douglasii* plants were greenhouse-grown and seeds collected at stages III and IV, as defined for *Limnanthes alba* by Laurent and Huang, Plant Physiol., 99: 1711–1715 (1992) (majority were stage IV). Total RNA was isolated by a standard hot SDS method and mRNA purified by oligo dT-cellulose chromatography using methods detailed in the manual accompanying Pharmacia mRNA purification kit. A cDNA library was made from 5 $\mu$g polyA+ RNA using a cDNA synthesis kit from Pharmacia. The cDNA was primed with oligo dT and cloned as EcoRI fragments into the phage vector lambda ZAPII. A plasmid-based cDNA library was made from an unamplified aliquot of the lambda library by plasmid rescue with the helper phage R408 using protocols described in Delauney and Verma, Plant Molecular Biology, Manual A14: 1–23 (1990). During construction, $1 \times 10^6$ colonies (=cDNA clones) were plated and scraped into LB medium. This was grown for 3 hr and a plasmid preparation carried out to get a cDNA library representative of $1 \times 10^6$ cDNA clones from developing mid to late stage Limnanthes embryos.

EXAMPLE 2

Isolation of Limnanthes '1' clone homologous to maize clone

The Limnanthes cDNA '1' clone was obtained by heterologous screening of a seed cDNA library using a 600 bp NcoI/PstI fragment of the rape 2AT clone described in WO-A-9413814. This fragment corresponds to the N-terminus of the rape protein. Plaque hybridisation was in 6xSSC, 1x Denhardts, 0.5% sodium pyrophosphate and 1 mM EDTA (pre-hybridisation in the same solution minus EDTA and plus 50 ug/ml denatured herring sperm DNA) and the filter was washed in 1xSSC at 60° C. The cDNA sequence of the hybridising clone (=pCB121) is shown in FIG. 1 (SEQ ID NO: 3). The relatedness between the rape (SEQ ID NO: 6), maize (SEQ ID NO: 5) and Limnanthes '1' (SEQ ID NO: 4) clones is shown in FIG. 2.

EXAMPLE 3

Rescue of complementing cDNA clone—Limnanthes '2'

Complementation of the 2-AT mutant JC201 was done with the plasmid library as described in Brown et al, *Plant Mol. Biol.*, 26: 211–223 (1994). 500 ng of DNA was used in the first transformation of the electroporation competent JC201, and after the second round of transformation with 50 ng of plasmid, substantially more colonies grew at 42° C. with the cDNA plasmids than with plasmid vector alone (pBS SK+). 18 of these colonies were picked at random and cDNA clones isolated from each one. All 18 clones had the same size EcoRI insert of 1.1 kb and one, designated pCB129, was used in further studies.

Sequencing of pCB129

The restriction sites of the 1.1 kb insert in pCB129 were mapped. Both cut and re-ligated plasmids and smaller insert fragments subcloned into pBS SK+ were used as sequencing templates to obtain the sequence shown in FIG. 3 (SEQ ID NO: 7).

EXAMPLE 4

Homologies to other acyltransferases

The 281 amino acid open reading frame starting at the first methionine was used as a probe sequence against the OWL database to search for homologous proteins. The top matches are shown in FIG. 4. The ORF is much more homologous to the 2-AT PLSC of *E. coli* than the maize sequence of pMAT1, disclosed in WO-A-9413814. The Limnanthes protein is 27% identical to the *E. coli* protein PlsC, and if a smaller fragment of the protein is aligned, the identity is 38% over a 141 amino acid stretch (see FIG. 6 (SEQ ID NO: 11 and SEQ ID NO: 12). An alignment with the top matching protein is in FIG. 7 (SEQ ID NO: 8 and SEQ ID NO: 13).

EXAMPLE 5

Northern blot analysis

The open reading frame from pCB129 was labelled with $^{32}$P and hybridised to a Northern Blot with 1 $\mu$g polyA+ RNA from Limnanthes embryo, leaf and stem at 42° C. and the blot washed with 0.1 x SSC 0.1% SDS at 42° C. The gene is predominantly expressed in the embryo, with very low levels of expression in leaf and stem (see FIG. 5).

EXAMPLE 6

Southern blot analysis

For the southern blots using plant DNAs, 2, 5 and 10 ug samples of *Arabidopsis thaliana*, *Limnanthes douglasii* and *Brassica napus* DNA were cut with BamHI, EcoRI and HindIII for separation and transfer. Hybridisations to all blots were done in the same hybridisation solution as described in example 2 above for the plaque hybridisation.

The Limnanthes '1' probe was a EcoRI/HindIII fragment of 1.3 kb and the blot was washed in 2xSSC at 60 C to give the results shown in FIG. 9*a* (higher stringency washes using 0.2xSSC at 60 C with another blot still left 5–6 bands per rape lane). Two blots with Limnanthes '2' probes were also carried out. The first need the EcoRI insert of pCB129 as a probe and was washed in 2xSSC at 60 C to give the results shown in FIG. 9*b*. The experiment was repeated with a probe corresponding to the ORF of pCB129, the result is shown in FIG. 9*c*.

It is clear that homologues in rape exist for Limnanthes '1' at high stringency, but not for Limnanthes '2'.

EXAMPLE 7

Substrate specificity assays

JP201 containing pCB129 was grown in 200 ml culture and membrane fractions collected after sonication of the bacteria to cause lysis. The membrane pellet was collected at 200000 g after two clearing spins of 16000 g. The resuspended membranes were used in single substrate assays together with membranes from JC200 bacteria, which are wild-type for 2-AT.

The LPA acceptor in these assays was $^{32}$P erucoyl LPA. This had been made from glycerol, [$\gamma^{32}$P]-ATP and erucoyl CoA using the enzymes glycerol kinase and over-produced 1-AT from arabidopsis (available in the lab). The LPA was purified from CoAs by thin layer chromatography on silica, extracted into methanol and resuspended in 0.2% octyl glucopyranoside after drying down.

For the assays, 100 $\mu$M LPA was used together with either 100 $\mu$M 18:1CoA or 100 $\mu$M 22:1CoA. Both JC200 and JC201 (pCB129) membranes were used separately in the assays. The experiment was repeated twice, with duplicate samples taken the first time and single samples taken at more time points the second. The results are shown in FIGS. 10 and 11. Shorter incubation times were used in the second experiment to try and get linear incorporation with time for at least two sample points to get more accurate values for initial velocities.

Addition of pCB129 to JC201 enables the membranes to utilise 22:1 CoAs much more effectively than wild-type *E. coli* membranes from JC200. In the second experiment, the ratios of 18:1 to 22:1 CoA incorporation after 5 minutes are 1.45:1 for Limnanthes complemented membranes and 3.38:1 for JC200 membranes (see FIG. 10 and 11).

EXAMPLE 8

Construction of a plant expression vector of pCB129. The putative ORF of the cDNA sequence described in FIG. 3 was cloned into the plant expression vector pAR4 (napin) promoter and chalcone synthase(CHS) terminator cassette in Bluescript (Stratagene). It was necessary to use PCR to engineer an NcoI site at the putative start codon of the ORF. To avoid the need to PCR the full ORF and hence to reduce the possibility of introducing errors into the sequence, a 280 bp fragment was synthesised by PCR and cloned as an XbaI/BamHI fragment into pCB130. pCB130 is a fully sequenced subclone of pCB129 with the 5' BamHI fragment deleted. The resulting clone was named pCB141. The approx. 880 by NcoI/SmaI fragment from pCB141 which encodes the putative ORF was excised and cloned into NcoI/SmI sites of pAR4 resulting in pCB143. The KbaI/HindIII fragment of pCB143 comprising napin promoter -2-AT ORF CHS terminator was ligated with BglII linkers and cloned into plasmid SCV1.2 (FIG. 12), resulting in SCV144. A second construct was developed by engineering an NcoI site approx. 100 bases downstream to allow translation to stat at the second methionine of the Limnanthes 2 clone. The vector was contructed in the same manner as the SCV114.

EXAMPLE 9

Introduction via Agrobacterium into oilseed rape

The SCV-based vector SCV144 (referred to in Example 8) carrying the putative ORF under the control of a seed specific promoter was introduced into *Agrobacterium tumefaciens*. The resulting Agrobacterium strain was used to transform cotyledonary peticles of high erucic acid oilseed rape essentially as described in Moloney et al. (Plant Cell Reports, 8:238–242 (1989)). SCV144 carries the neomycin phosphotransferase (NPTII) gene allowing transformants to develop in the presence of the antibiotic kanamycin. Two transformation experiments (1000 cotyledons) were carried out.

Regenerant plants were grown to the four leaf stage and screened by polymerase chain reaction for the presence of the NPTII gene. The following primers were employed:

TN5 KAN1: 5' CGCAGGTTCTCCGGCGGCT-TGGGTGG 3' (SEQ ID NO:1) (26 bases);

TN5 KAN2: 5' AGCAGCCAGTCCCTTCCCGCTTCAG 3' (SEQ ID NO:2)(25 bases).

The buffer employed was as follows:

$$10X = 100 \text{ mM TMS pH } 8.8$$

$$500 \text{ mM KCl}$$

$$15 \text{ mM MgCl}_2$$

$$1\% \text{ Triton } X100$$

The following protocol was employed:
30 cycles of
a) 20 secs at 97.5° C.
b) 30 secs at 65° C.
c) 90 secs at 74° C.

1 cycle of 5 mins at 72° C. and a slow decrease to room temp. The results are shown in FIG. 13.

Fifty NPTII +ve plants were then grown to maturity and analysed by Southern blot for the presence of the sequence referred to in Example 3.

A microsome fraction was isolated from developing seeds. The tissue was homogenised with a polytron and the membrane fraction collected as a 200000 g pellet after a clearing spin of 40000 g. The membranes were washed with 0.5 M salt to remove extrinsic membrane proteins, and pelleted again at 200000 g before storage at −80° C.

The assays were carried out separately with 50 $\mu$M 18:1 LPA and 22:1 PA and 100 $\mu$M 18:1CoA or 22:1CoA as acyl donors. The microsomes were capable of incorporating 22:1 CoA at position 2 of 1-acyl-glycerol-3-phosphate. Control microsomes from HEAR oilseed rape were unable to carry out this reaction.

Seed from 10 plane carrying the gene were analysed for the presence of trierucin molecules (see Taylor et al., *J. Am. Oil. Chem. Soc.*, 69: 355–358 (1992) for analysis of trierucin content, and Christie. *Lipid Analysis, 2nd Edn., Pergamon Press,* Toronto, Canada: 158–161 (1982) for determination of amount of erucic acid at the 2-position) and for the level of erucic acid in the seed oil. A range of levels of trierucin were evident (and the results are shown in table 1), whereas none is found in the untransformed line, and among the regenerants, some plants are found with levels of erucic acid over the level which is normally found in the HEAR untransformed line.

TABLE 1

| Plant Number | % trierucin |
|---|---|
| 1 | 0.03 |
| 2 | 2.8 |
| 3 | 0.4 |
| 4 | 2.9 |

TABLE 1-continued

| Plant Number | % trierucin |
|---|---|
| 5 | 2.7 |
| 6 | 0.01 |
| 7 | 2.1 |
| 8 | 1.0 |
| 9 | 0.1 |
| 10 | 1.4 |
| control | 0.0 |

EXAMPLE 10

TAG extraction:

Nature seeds were collected from transgenic plants. The seeds wre then extracted by homogenization with isopropanol (2 ml) and then hexane (5 ml). The extracts were filtered, the solvent was evaporated in a stream of nitrogen and the TAGs were taken up in acetone-acetonitrile (1:1, v/v; 1 ml) containing BHT (50 mg/ml), and were stored at 4° C. until analysed.

TABs were analysed by reverse-phase high-performance liquid chromatography with a Gynkotek Model 480 pump and a Varex Model III evaporative light-scattering detector. The column consisted of two ChromSpher C18 (100×4.6 mm; 3 micron particles) cartridge columns in series with guard column. The mobile phase was acetone-acetonitrile (1:1, v/v) and 10 $\mu$l injected onto the column. With this system, trerucin eluted in approximately 17–20 minutes.

Gas chromatography:

Methyl esters of fatty acids were prepared by sodium methoxide-catalysed transesterification (Christie, W. W., *Gas Chromatography and Lipids,* Dundee, the oily press (1989)). They were analyzed on a Hewlett Packard Model 5890 Series II gas chromatograph, fitted with split/splitless injection, and equipped with a capillary column (25 m×0.25 mm×0.2 mm film thickness) of fused silica coated with CP-Wax 52CB. The carrier gas was hydrogen at a flow rate of 1 ml/min. The initial temperature in the column was 170° C. for 3 min, then the temperature was programmed to 210° C. at 4° C./min. and held at this point for a further 25 min. Components were quantified by electronic integration.

Mass spectrometry:

The component co-chromatographing with trierucin was collected and pooled from five micropreparative HPLC runs under essentially the conditions described above. After removal of the solvent, the lipid in hexane solution was inserted via a syringe pump directly into the Finnigan SSQ 710C mass spectrometer with atmospheric pressure chemical ionization (APCI) at a corona voltage of 5.07 kV.

Pancreatic lipase hyrolysis:

TAGs were subjected to pancreatic lipase hydrolysis by the method of Luddy et al. (*J. Am. Oil Chem. Soc.,* 41:693–696 (1964)). 1M Tris buffer (1 ml, pH 8), calcium chloride solution (0.1 ml; 2.2%) and bile salt solution (0.25 ml; 0.05%) were added to the TAGs (5 mg) and these were hydrolysed with pancreatic lipase (pig pancreatin, Sigma) at 40° C. for 2 min. The reaction was stopped by the addition of ethanol (1 ml) followed by 6M hydrochloric acid (1 ml), and the solution extracted three times with diethyl ether (4 ml portions). The solvent layer was washed once with distilled water (3 ml) and dried with sodium sulphate, before the solvent was removed on a rotary evaporator.

The required 2-monoacylglycerol products were isolated by micro-preparative HPLC on silica gel, ie. a column of Hypersil H# (250×4.6 mm). A Spectra-Physics Model 8700 solvent delivery system was used together with a Cunow Model) DDL21 light-scattering detector (Severn Analytical). A stream-splitter (approximately 10:1) was inserted between the column and the detector to permit collection of fractions, the mobile phase was isohexane-methylterbutyl ether-acetic acid 100:100:0.02 by volume) at a flow rate of 1 ml/min. Monoacylglycerole eluted after about 14 min and were collected manually via the stream-splitter. They were methylated for GC analysis as before.
Results:

HPLC analysis of TAG

To initially identify plants which were expressing the Limnanthes LPA-AT protein, mature seed from transgenic plants was analysed for the presence of trierucin. The TAG fraction was extracted and examined by reverse-phase HPLC (FIG. 14).

Using this system trierucin was eluted at aprox. 17–20 mins; FIG. 14A shows analysis of non-transformed *B. napus* in which no trierucin was detected. However, transgenic plants SCV144-2 and SCV144-9 were found to have 2.8% and 0.4%, respectively, of a lipid species which eluted at the same retention time as trierucin (FIGS. 14B and C). A slight difference in the retention time for trierucin is apparent between the chromatograms illustrated in FIG. 14 as these were run on different occasions under slightly different conditions, but for each run the position of the trierucin peak was assigned by calibration with authentic trierucin.

The separation of the lipid species achieved by reverse-phase HPLC depends partly on the chain length and partly on the degree of unsaturation of the molecule. The elution time increases with the total number of carbon atoms in the fatty acid chain but is decreased by roughly the equivalent of 2C for each double bond. Therefore a TAG of C20:1-C22:1-C22:1 could elute in a similar but not identical place as trierucin (C22:1-C22:1-C22:1); trierucin would not be distinguished from C20:1-C22:1-C24:1, if this TAG were also present. The results obtained strongly imply that erucic acid was being incorporated at sn-2 but for absolute confirmation of the identity of the trierucin peak mass spectrometry analysis was performed.

Figure 15A:
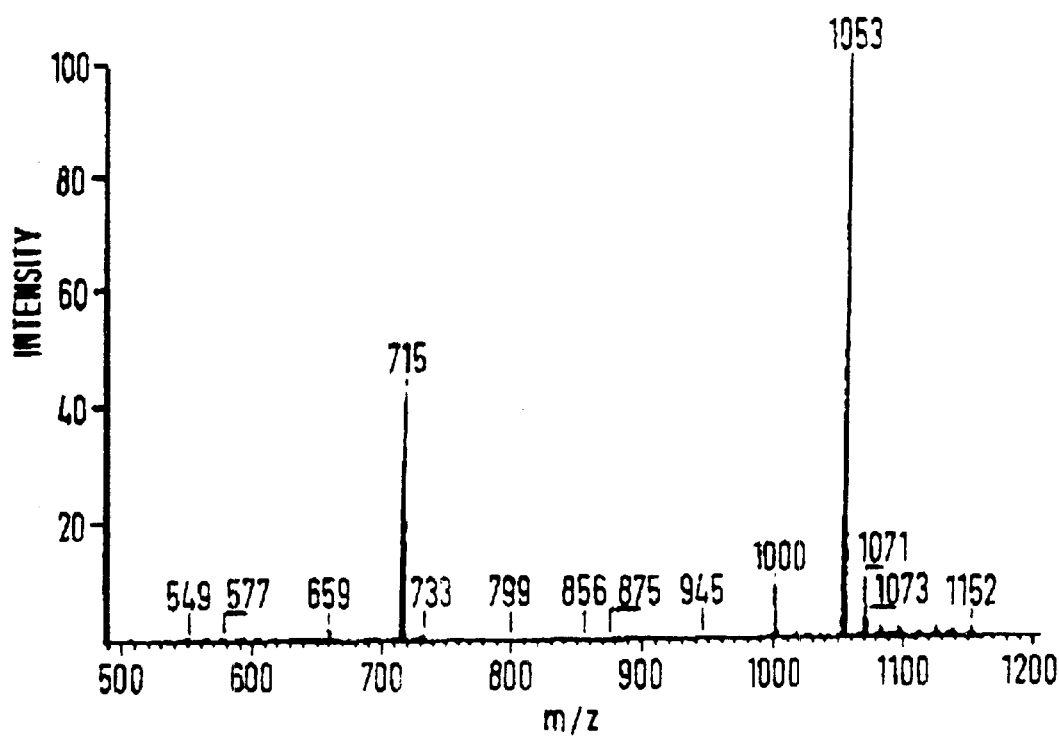
Figure 15B:
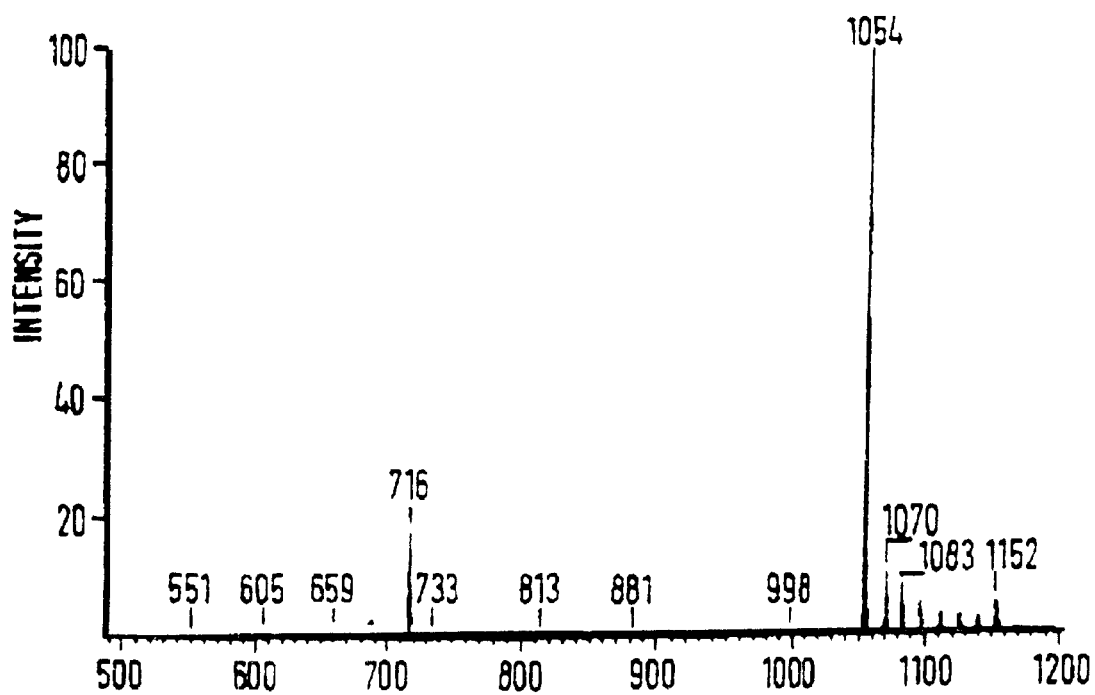

Mass spectral assignment of trierucin:

The components from seeds of SCV144-2 and SCV144-9 which co-chromatographed with trierucin were collected and pooled from five micropreparation HPLC runs and subjected to mass spectral analysis. FIG. 15A shows the spectrum of authentic trierucin and FIG. 15B that from transgenic seed of SCV144-9. The most abundant ion at m/z 1053.5 (labelled as 1053 and 1054 in (A) and (B) respectively) is the molecular ion [M+] for trierucoylglycerol. The ion at 715/716 represents loss of an erucate moiety. The results confirm the presence of trierucin and hence demonstrate that erucic acid was incorporated at sn-2 of TAG in the transgenic rape plants.

Fatty acid analysis of TAG:

The transgenic plants SCV144-2 and SCV144-9 were found to have only low levels of trierucin (2.8% and 0.4% respectively). Therefore to determine if the incorporation of erucic acid at the sn-2 position was limiting the production of trierucin, detailed positional analysis of fatty acids in TAG was performed. Total fatty acid composition was determined by gas chromatography (GC) of methyl esters. The identity of fatty acids at position 2 was determined by initial treatment of TAG with pancreatic lipase which removes the acyl groups from sn-1 and sn-3. The desired 2-monoacylglycerol products were isolated by micropreparation HPLC then methylated and examined by GC.

Under the growth conditions used the starting population had a maximum of 31.7 mol % erucic acid in the seed oil. Analysis of selected non-transformed rape plants showed that no erucic acid was incorporated at the 2 position. However, in SCV144-9 which had 0.4% trierucin and an erucic acid level of 32.2 mol %. erucic acid made up 9 mol % of the fatty acids esterified at sn-2. Similarly, in SCV144-2 which had 2.8% trierucin, erucic acid manes up 32.1 mol % of total TAG fatty acids and 28.3 mol % of fatty acids esterified at sn-2. In these transgenic plants the amount of erucic acid at sn-2 appears to be corrrelated with the trierucin content.

What is claimed is:

1. An isolated DNA molecule comprising nucleotides having a nucleotide sequence selected from the group consisting of:
   (i) a nucleotide sequence encoding the amino acid sequence shown in SEQ ID NO: 8; and
   (ii) a nucleotide sequence identical to the sequence of nucleotides 10–297 of SEQ ID NO: 7, or its complement.

2. The isolated DNA molecule of claim 1 encoding the same amino acid sequence as a DNA molecule comprising nucleotides having the nucleotide sequence of SEQ ID NO: 7.

3. The isolated DNA molecule of claim 1 comprising nucleotides having the nucleotide sequence of SEQ ID NO: 7 or its complement.

4. A transgenic plant which is B. napus, B. campestris, B. juncea or B. rapa, which plant is transgenic because it includes in its genome a DNA molecule comprising nucleotides having a nucleotide sequence selected from the group consisting of:
   (i) a nucleotide sequence encoding the amino acid sequence shown in SEQ ID NO: 8;
   (ii) a nucleotide sequence identical to the sequence of nucleotides 10–297 of SEQ ID NO: 7, or its complement;
   (iii) a nucleotide sequence encoding an enzyme having membrane-bound acyltransferase activity, which DNA molecule hybridizes to the complement of nucleotides 10-297 of SEQ ID NO: 7 under stringent conditions; and
   (iv) a nucleotide sequence that hybridizes along the full length of the DNA sequence of SEQ ID NO: 7 of its complement under stringent conditions;
   wherein the DNA molecule encodes a 2-acyltransferase enzyme and is not endogenous to the plant.

5. The plant as claimed in claim 4, wherein the nucleotide sequence encodes the amino acid sequence shown in SEQ ID NO: 8.

6. The plant as claimed in claim 5, wherein the nucleotide sequence encodes an enzyme having membrane-bound 2-acyltransferase activity.

7. A plant cell of B. napus, B. campestris, B. juncea or B. rapa comprising a 2-acyltransferase gene, which gene is not endogenous to the plant species, wherein the plant cell is obtained from a plant as defined in claim 4.

8. A seed comprising a 2-acyltransferase gene which gene is not endogenous to the plant species, wherein the seed is obtained from a plant as defined in claim 4.

9. A seed comprising a 2-acyltransferase gene which gene is not endogenous to the plant species, wherein the seeds is obtained from a plant as defined in claim 5.

10. A method of generating oil comprising cultivating the transgenic plant of claim 4 and harvesting oil produced by the plant or a part of the plant.

11. The method of claim 10, wherein the part of the plant from which the oil is harvested is seeds from the plant.

12. The isolated DNA molecule of claim 1, wherein the DNA molecule is capable of complementing a mutation in an E. coli gene coding for a defective 2-acyltransferase.

13. The isolated DNA molecule of claim 1, comprising nucleotides having a sequence identical to the sequence of nucleotides 10-297 of SEQ ID NO: 7, or its complement.

14. A transgenic plant which plant is transgenic because it includes in its genome a DNA molecule comprising nucleotides having a nucleotide sequence selected from the group consisting of:
  (i) a nucleotide sequence encoding the amino acid sequence shown in SEQ ID NO: 8;
  (ii) a nucleotide sequence identical to the sequence of nucleotides 10-297 of SEQ ID NO: 7, or its complement;
  (iii) a nucleotide sequence encoding an enzyme having membrane-bound acyltransferase activity, which DNA molecule hybridizes to the complement of nucleotides 10-297 of SEQ ID NO: 7 under stringent conditions; and
  (iv) a nucleotide sequence that hybridizes along the full length of the DNA sequence of SEQ ID NO: 7 or its complement under stringent conditions;
  wherein the DNA molecule encodes a 2-acyltransferase enzyme and is not endogenous to the plant.

15. The transgenic plant of claim 14 selected from the group consisting of *B. napus, B. campestris, B. junces* or *B. rapa*.

16. The transgenic plant of claim 14, wherein the nucleotide sequence encodes the amino acid sequence shown in SEQ ID NO: 8.

17. The plant of claim 14, wherein the nucleotide sequence encodes an enzyme having membrane-bound 2-acyltransferase activity.

18. The plant of claim 15, the plant having higher levels of erucic acid incorporated into triacylglycerols than non-transgenic equivalents.

19. The plant of claim 15, the plant having erucic acid incorporated at the sn-2 position of in-seed triacylglycerols (TAGs).

20. The plant of claim 15, which contains trierucin.

21. The plant of claim 19, which contains trierucin.

22. A transgenic seed comprising a 2-acyltransferase gene which gene is not endogenous to the plant species, the seed obtained from a plant as defined in claim 20.

23. The seed of claim 22, the seed containing trierucin.

24. The seed of claim 23, wherein the concentration of trierucin is enhanced relative to the concentration of trierucin in a seed from a corresponding non-transgenic plant.

25. The seed of claim 23, having triacylglycerols comprising trierucin at a concentration of 2.1%.

26. The seed of claim 25, having triacylglycerols comprising trierucin at a concentration of 2.9%.

27. A method of generating oil comprising cultivating a plant claimed in claim 14 and harvesting oil produced by the plant or a part of the plant.

28. The method as claimed in claim 27, wherein the oil is harvested from the seeds of the plant.

29. A transgenic *B. napus* plant which plant is transgenic because it includes in its genome a DNA molecule comprising nucleotide having a nucleotide sequence selected from the group consisting of:
  (i) a nucleotide sequence encoding the amino acid sequence shown in SEQ ID NO: 8;
  (ii) a nucleotide sequence identical to the sequence of nucleotides 10-297 of SEQ ID NO: 7, or its complement;
  (iii) a nucleotide sequence encoding an enzyme having membrane-bound acyltransferase activity, which DNA molecule hybridizes to the complement of nucleotides 10-297 of SEQ ID NO: 7 under stringent conditions; and
  (iv) a nucleotide sequence that hybridizes along the full length of the DNA sequence of SEQ ID NO: 7 or tis complement under stringent conditions;
  wherein the DNA molecule encodes a 2-acyltransferase enzyme and is not endogenous to the *B. napus* plant.

30. A transgenic seed comprising a 2-acyltransferase gene which gene is not endogenous to the plant species, the seed obtained from the *B. napus* plant of claim 29.

31. The seed of claim 30, the seed containing trierucin.

32. The seed of claim 31, wherein the concentration of trierucin is enhanced relative to the concentration of trieurcin in a seed from a corresponding non-transgenic *B. napus* plant.

33. The seed of claim 30, having triacylglycerols comprising 28.3 mol % erucic acid of the fatty acids esterified at the sn-2 position.

34. A transgenic seed comprising a 2-acyltransferase gene which gene is not endogenous to the plant species, the seed obtained from a plant as defined in claim 14.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 1:

CGCAGGTTCT CCGGCGGCTT GGGTGG                                              26

(2) INFORMATION FOR SEQ ID NO: 2:

(i) SEQUENCE CHARACTERISTICS:
       (A) LENGTH: 25 base pairs
       (B) TYPE: nucleic acid
       (C) STRANDEDNESS: single (D) TOPOLOGY: linear (ii) MOLECULE TYPE: cDNA (xi) SEQUENCE DESCRIPTION: SEQ ID NO: 2:

```
AGCAGCCAGT CCCTTCCCGC TTCAG                                       25
```

(2) INFORMATION FOR SEQ ID NO: 3:

(i) SEQUENCE CHARACTERISTICS:
        (A) LENGTH: 1515 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:182..1316

(xi) SEQUENCE DESCRIPTION: SEQ ID NO: 3:

```
GAATTCGCGG CCGCTACCGG CCATTCTAAT TTTATATCCA AACGCCCCTC TCCATCTTCC    60

TCGATTCATT TTTCTCGATC TTTCATCTTT TCCTACCATT CCTCTCTCTA CAACATTCTT   120

TTACACTATA CATCCTTAGA GCTTCTCTTC CCTCATCGTT ATAGCCCGAG CTAAAGCTGC   180
```

```
C ATG GCG ATC CCT GCT GCA GCT TTC ATC GTA CCA ATA AGT CTT CTT      226
  Met Ala Ile Pro Ala Ala Ala Phe Ile Val Pro Ile Ser Leu Leu
  1               5                  10                  15

TTT TTC ATG TCA GGC CTC GTT GTC AAT TTC ATT CAG GCA GTC TTC TAT    274
Phe Phe Met Ser Gly Leu Val Val Asn Phe Ile Gln Ala Val Phe Tyr
                20                  25                  30

GTT CTT GTT CGG CCT ATT TCT AAG GAC ACA TAC AGA AGG ATC AAT ACG    322
Val Leu Val Arg Pro Ile Ser Lys Asp Thr Tyr Arg Arg Ile Asn Thr
            35                  40                  45

TTG GTG GCA GAA TTG TTG TGG CTA GAA CTT GTA TGG GTC ATT GAT TGG    370
Leu Val Ala Glu Leu Leu Trp Leu Glu Leu Val Trp Val Ile Asp Trp
        50                  55                  60

TGG GCA GGC GTT AAG GTC CAA TTA TAT ACT GAT ACT GAG TCT TTC CGT    418
Trp Ala Gly Val Lys Val Gln Leu Tyr Thr Asp Thr Glu Ser Phe Arg
    65                  70                  75

CTA ATG GGT AAA GAA CAT GCA CTC TTA ATA TGC AAC CAC AGA AGT GAC    466
Leu Met Gly Lys Glu His Ala Leu Leu Ile Cys Asn His Arg Ser Asp
80                  85                  90                  95

ATT GAC TGG CTC ATT GGA TGG GTC CTA GCA CAG CGA TGC GGC TGC CTC    514
Ile Asp Trp Leu Ile Gly Trp Val Leu Ala Gln Arg Cys Gly Cys Leu
                100                 105                 110

AGT TCT TCA ATA GCT GTT ATG AAG AAG TCA TCC AAA TTT CTC CCG GTA    562
Ser Ser Ser Ile Ala Val Met Lys Lys Ser Ser Lys Phe Leu Pro Val
            115                 120                 125

ATA GGT TGG TCT ATG TGG TTT TCC GAA TAT CTC TTT CTC GAG AGG AAC    610
Ile Gly Trp Ser Met Trp Phe Ser Glu Tyr Leu Phe Leu Glu Arg Asn
        130                 135                 140

TGG GCC AAA GAT GAA AAC ACT TTA AAG TCA GGT CTC CAG CGG CTG AAT    658
Trp Ala Lys Asp Glu Asn Thr Leu Lys Ser Gly Leu Gln Arg Leu Asn
145                 150                 155

GAC TTC CCT AAG CCT TTT TGG TTA GCT CTG TTT GTG GAA GGA ACT CGT    706
Asp Phe Pro Lys Pro Phe Trp Leu Ala Leu Phe Val Glu Gly Thr Arg
160                 165                 170                 175

TTC ACG AAA GCA AAA CTT CTA GCT GCT CAG GAA TAT GCA GCC TCT GCA    754
Phe Thr Lys Ala Lys Leu Leu Ala Ala Gln Glu Tyr Ala Ala Ser Ala
                180                 185                 190
```

```
GGA TTA CCC GTG CCT CGA AAT GTT CTG ATT CCT CGT ACG AAG GGC TTT        802
Gly Leu Pro Val Pro Arg Asn Val Leu Ile Pro Arg Thr Lys Gly Phe
            195                 200                 205

GTG TCA GCC GTT AGT AAC ATG CGC TCA TTT GTC CCA GCT ATC TAT GAC        850
Val Ser Ala Val Ser Asn Met Arg Ser Phe Val Pro Ala Ile Tyr Asp
                210                 215                 220

TTG ACA GTC GCC ATT CCT AAA ACC ACG GAA CAA CCT ACA ATG CTC AGA        898
Leu Thr Val Ala Ile Pro Lys Thr Thr Glu Gln Pro Thr Met Leu Arg
        225                 230                 235

CTG TTC AGG GGG AAA TCT TCT GTG GTA CAC GTA CAC CTT AAG CGG CAT        946
Leu Phe Arg Gly Lys Ser Ser Val Val His Val His Leu Lys Arg His
240                 245                 250                 255

TTG ATG AAG GAC TTG CCT AAA ACA GAT GAC GGT GTT GCA CAG TGG TGT        994
Leu Met Lys Asp Leu Pro Lys Thr Asp Asp Gly Val Ala Gln Trp Cys
                260                 265                 270

AAA GAT CAA TTT ATA TCC AAG GAT GCA TTG TTA GAC AAA CAT GTT GCT       1042
Lys Asp Gln Phe Ile Ser Lys Asp Ala Leu Leu Asp Lys His Val Ala
        275                 280                 285

GAG GAT ACT TTC AGT GGC CTG GAA GTG CAG GAC ATT GGT CGG CCA ATG       1090
Glu Asp Thr Phe Ser Gly Leu Glu Val Gln Asp Ile Gly Arg Pro Met
                290                 295                 300

AAG TCT CTT GTG GTG GTT GTC TCG TGG ATG TGC CTA CTC TGT TTG GGG       1138
Lys Ser Leu Val Val Val Val Ser Trp Met Cys Leu Leu Cys Leu Gly
305                 310                 315

CTT GTG AAA TTT CTT CAG TGG TCA GCA CTT TTA TCC TCA TGG AAG GGT       1186
Leu Val Lys Phe Leu Gln Trp Ser Ala Leu Leu Ser Ser Trp Lys Gly
320                 325                 330                 335

ATG ATG ATA ACG ACA TTC GTT CTG GGA ATC GTG ACC GCC CTT ATG CAC       1234
Met Met Ile Thr Thr Phe Val Leu Gly Ile Val Thr Ala Leu Met His
                340                 345                 350

ATC TTG ATA CGT TCT TCC CAG TCA GAG CAT TCA ACC CCG GCA AAG ACG       1282
Ile Leu Ile Arg Ser Ser Gln Ser Glu His Ser Thr Pro Ala Lys Thr
        355                 360                 365

AGG GCC AGA CAA ACT GCA GAG AAC CCA AAA TGA A ATAAGCTTTT              1326
Arg Ala Arg Gln Thr Ala Glu Asn Pro Lys
370                 375

TTTCTTTATT AACGAACGGT ATATCATATG TAGTAATGTG GGTTTCCTTC ATTTACCAAT     1386

GGATTTATGT TATCAATGCG GAAGAATTAA GATGTTTTTT TTTGCCTTCC GGAGTTGTTT     1446

TACTGTATAG ACTTGTATGC TGAATATGCA CAATTAGAGA TATGTCATTG TTTTAGCGGC     1506

CGCGAATTC                                                             1515

(2) INFORMATION FOR SEQ ID NO: 4:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Ile Pro Ala Ala Phe Ile Val Pro Ile Ser Leu Leu Phe
  1               5                  10                  15

Phe Met Ser Gly Leu Val Val Asn Phe Ile Gln Ala Val Phe Tyr Val
                 20                  25                  30

Leu Val Arg Pro Ile Ser Lys Asp Thr Tyr Arg Arg Ile Asn Thr Leu
             35                  40                  45

Val Ala Glu Leu Leu Trp Leu Glu Leu Val Trp Val Ile Asp Trp Trp
         50                  55                  60
```

```
Ala Gly Val Lys Val Gln Leu Tyr Thr Asp Thr Glu Ser Phe Arg Leu
 65                  70                  75                  80

Met Gly Lys Glu His Ala Leu Leu Ile Cys Asn His Arg Ser Asp Ile
                 85                  90                  95

Asp Trp Leu Ile Gly Trp Val Leu Ala Gln Arg Cys Gly Cys Leu Ser
            100                 105                 110

Ser Ser Ile Ala Val Met Lys Lys Ser Ser Lys Phe Leu Pro Val Ile
        115                 120                 125

Gly Trp Ser Met Trp Phe Ser Glu Tyr Leu Phe Leu Glu Arg Asn Trp
130                 135                 140

Ala Lys Asp Glu Asn Thr Leu Lys Ser Gly Leu Gln Arg Leu Asn Asp
145                 150                 155                 160

Phe Pro Lys Pro Phe Trp Leu Ala Leu Phe Val Glu Gly Thr Arg Phe
                165                 170                 175

Thr Lys Ala Lys Leu Leu Ala Ala Gln Glu Tyr Ala Ala Ser Ala Gly
            180                 185                 190

Leu Pro Val Pro Arg Asn Val Leu Ile Pro Arg Thr Lys Gly Phe Val
        195                 200                 205

Ser Ala Val Ser Asn Met Arg Ser Phe Val Pro Ala Ile Tyr Asp Leu
210                 215                 220

Thr Val Ala Ile Pro Lys Thr Thr Glu Gln Pro Thr Met Leu Arg Leu
225                 230                 235                 240

Phe Arg Gly Lys Ser Ser Val Val His Val His Leu Lys Arg His Leu
                245                 250                 255

Met Lys Asp Leu Pro Lys Thr Asp Asp Gly Val Ala Gln Trp Cys Lys
            260                 265                 270

Asp Gln Phe Ile Ser Lys Asp Ala Leu Leu Asp Lys His Val Ala Glu
        275                 280                 285

Asp Thr Phe Ser Gly Leu Glu Val Gln Asp Ile Gly Arg Pro Met Lys
290                 295                 300

Ser Leu Val Val Val Ser Trp Met Cys Leu Leu Cys Leu Gly Leu
305                 310                 315                 320

Val Lys Phe Leu Gln Trp Ser Ala Leu Leu Ser Ser Trp Lys Gly Met
                325                 330                 335

Met Ile Thr Thr Phe Val Leu Gly Ile Val Thr Ala Leu Met His Ile
            340                 345                 350

Leu Ile Arg Ser Ser Gln Ser Glu His Ser Thr Pro Ala Lys Thr Arg
        355                 360                 365

Ala Arg Gln Thr Ala Glu Asn Pro Lys
370                 375
```

(2) INFORMATION FOR SEQ ID NO: 5:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Zea mays (xi) SEQUENCE DESCRIPTION: SEQ ID NO: 5:

```
Met Ala Ile Pro Leu Val Leu Val Val Leu Pro Leu Gly Leu Leu Phe
1                5                  10                  15
```

```
Leu Leu Ser Gly Leu Ile Val Asn Ala Ile Gln Ala Val Leu Phe Val
             20                  25                  30

Thr Ile Arg Pro Phe Ser Lys Ser Phe Tyr Arg Arg Ile Asn Arg Phe
         35                  40                  45

Leu Ala Glu Leu Leu Trp Leu Gln Leu Val Trp Val Asp Trp Trp
 50                  55                  60

Ala Gly Val Lys Val Gln Leu His Ala Asp Glu Thr Tyr Arg Ser
 65              70                  75                  80

Met Gly Lys Leu His Ala Leu Ile Ile Ser Asn His Arg Ser Asp Ile
                 85                  90                  95

Asp Trp Leu Ile Gly Trp Ile Leu Ala Gln Arg Ser Gly Cys Leu Gly
             100                 105                 110

Ser Thr Leu Ala Val Met Lys Lys Ser Ser Lys Phe Leu Pro Val Ile
             115                 120                 125

Gly Trp Ser Met Trp Phe Ala Glu Tyr Leu Phe Leu Glu Arg Ser Trp
             130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
             165                 170                 175

Thr Pro Ala Lys Leu Leu Ala Ala Gln Glu Tyr Ala Ala Ser Gln Gly
             180                 185                 190

Leu Pro Ala Pro Arg Asn Val Leu Ile Pro Arg Thr Lys Gly Phe Val
             195                 200                 205

Ser Ala Val Ser Ile Met Arg Asp Phe Val Pro Ala Ile Tyr Asp Thr
             210                 215                 220

Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                 245                 250                 255

Met Ser Glu Met Pro Lys Ser Asp Glu Asp Val Ser Lys Trp Cys Lys
             260                 265                 270

Asp Ile Phe Val Ala Lys Asp Ala Leu Leu Asp Lys His Leu Ala Thr
             275                 280                 285

Gly Thr Phe Asp Glu Glu Ile Arg Pro Ile Gly Arg Pro Val Lys Ser
             290                 295                 300

Leu Leu Val Thr Leu Phe Trp Ser Cys Leu Leu Leu Phe Gly Ala Ile
305                 310                 315                 320

Glu Phe Phe Lys Trp Thr Gln Leu Leu Ser Thr Trp Arg Gly Val Ala
             325                 330                 335

Phe Thr Ala Ala Gly Met Ala Leu Val Thr Gly Val Met His Val Phe
             340                 345                 350

Ile Met Phe Ser Gln Ala Glu Arg Ser Ser Ser Ala Arg Ala Ala Arg
             355                 360                 365

Asn Arg Val Lys Lys Glu Xaa
             370                 375

(2) INFORMATION FOR SEQ ID NO: 6:

(i) SEQUENCE CHARACTERISTICS:
        (A) LENGTH: 311 amino acids
        (B) TYPE: amino acid
        (C) STRANDEDNESS: single
        (D) TOPOLOGY: linear
```

```
        (ii) MOLECULE TYPE: protein (vi) ORIGINAL SOURCE:
             (A) ORGANISM: Brassica napus (xi) SEQUENCE DESCRIPTION: SEQ ID NO: 6:

Met Ala Met Ala Ala Val Ile Val Pro Leu Gly Ile Leu Phe Phe
1               5                   10                  15

Ile Ser Gly Leu Val Val Asn Leu Leu Gln Arg Ser Gly Cys Leu Gly
            20                  25                  30

Ser Ala Leu Ala Val Met Lys Lys Ser Ser Lys Phe Leu Pro Val Ile
            35                  40                  45

Gly Trp Ser Met Trp Phe Ser Glu Tyr Leu Phe Leu Glu Arg Asn Trp
50                      55                  60

Ala Lys Asp Glu Ser Thr Leu Lys Ser Gly Leu Gln Arg Leu Asn Asp
65                  70                  75                  80

Phe Pro Arg Pro Phe Trp Leu Ala Leu Phe Val Glu Gly Thr Arg Phe
                85                  90                  95

Thr Glu Ala Lys Leu Lys Ala Ala Gln Glu Tyr Ala Ala Ser Ser Glu
            100                 105                 110

Leu Pro Val Pro Arg Asn Val Leu Ile Pro Arg Thr Lys Gly Phe Val
            115                 120                 125

Ser Ala Val Ser Asn Met Arg Ser Phe Val Pro Ala Ile Tyr Asp Met
130                 135                 140

Thr Val Ala Ile Pro Lys Thr Ser Pro Pro Thr Met Leu Arg Leu
145                 150                 155                 160

Phe Lys Gly Gln Pro Ser Val Val His Val His Ile Lys Cys His Ser
                165                 170                 175

Met Lys Asp Leu Pro Glu Ser Glu Asp Glu Ile Ala Gln Trp Cys Arg
            180                 185                 190

Asp Gln Phe Val Thr Lys Asp Ala Leu Leu Asp Lys His Ile Ala Ala
            195                 200                 205

Asp Thr Phe Ala Gly Lys Gln Asn Ile Gly Arg Pro Ile Lys
            210                 215                 220

Ser Leu Ala Val Val Leu Ser Trp Ala Cys Leu Leu Thr Leu Gly Ala
225                 230                 235                 240

Met Lys Phe Leu His Trp Ser Asn Leu Phe Ser Ser Trp Lys Gly Ile
                245                 250                 255

Ala Leu Ser Ala Leu Gly Leu Gly Ile Ile Thr Leu Cys Met Gln Ile
            260                 265                 270

Leu Ile Arg Ser Ser Gln Ser Glu Arg Ser Thr Pro Ala Lys Val Ala
            275                 280                 285

Pro Ala Lys Pro Lys Asp Asn His Gln Ser Gly Pro Ser Ser Gln Thr
290                 295                 300

Glu Val Glu Glu Lys Gln Lys
305                 310

(2) INFORMATION FOR SEQ ID NO: 7:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
```

(A) ORGANISM: Limnanthes douglasii
(B) STRAIN: pCB129

(ix) FEATURE:
    (A) NAME/KEY: CDS
    (B) LOCATION:10..855

(xi) SEQUENCE DESCRIPTION: SEQ ID NO: 7:

| | | | | | | | | | | | | | |
|---|---|---|---|---|---|---|---|---|---|---|---|---|---|
| GTTCTATTC | ATG | GCC | AAA | ACT | AGA | ACT | AGC | TCT | CTC | CGC | AAC | AGG | AGA | 48 |
| | Met | Ala | Lys | Thr | Arg | Thr | Ser | Ser | Leu | Arg | Asn | Arg | Arg | |
| | | | | 380 | | | | 385 | | | | 390 | | |

```
GTTCTATTC ATG GCC AAA ACT AGA ACT AGC TCT CTC CGC AAC AGG AGA           48
          Met Ala Lys Thr Arg Thr Ser Ser Leu Arg Asn Arg Arg
              380             385                 390

CAA CTA AAG CCG GCT GTA GCT GCT ACT GCT GAT GAT GAT AAA GAT GGG         96
Gln Leu Lys Pro Ala Val Ala Ala Thr Ala Asp Asp Asp Lys Asp Gly
            395             400             405

GTT TTT ATG GTA TTG CTA TCG TGT TTC AAA ATT TTT GTT TGC TTT GCG        144
Val Phe Met Val Leu Leu Ser Cys Phe Lys Ile Phe Val Cys Phe Ala
            410             415             420

GTA GTG TTG ATC ACG GCG GTG GCA TGG GGA CTA ATC ATG GTC CTG CTC        192
Val Val Leu Ile Thr Ala Val Ala Trp Gly Leu Ile Met Val Leu Leu
            425             430             435

TTA CCT TGG CCT TAT ATG AGG ATT CGA CTA GGA AAT CTT TAC GGC CAT        240
Leu Pro Trp Pro Tyr Met Arg Ile Arg Leu Gly Asn Leu Tyr Gly His
440             445             450             455

ATC ATT GGT GGA TTA GTG ATA TGG ATT TAC GGA ATA CCA ATA AAG ATC        288
Ile Ile Gly Gly Leu Val Ile Trp Ile Tyr Gly Ile Pro Ile Lys Ile
            460             465             470

CAA GGA TCC GAG CAT ACA AAG AAG AGG GCC ATT TAT ATA AGC AAT CAT        336
Gln Gly Ser Glu His Thr Lys Lys Arg Ala Ile Tyr Ile Ser Asn His
            475             480             485

GCT TCT CCT ATC GAT GCT TTC TTT GTT ATG TGG TTG GCT CCC ATA GGC        384
Ala Ser Pro Ile Asp Ala Phe Phe Val Met Trp Leu Ala Pro Ile Gly
            490             495             500

ACA GTT GGT GTT GCA AAG AAA GAG GTT ATA TGG TAT CCG CTA CTT GGA        432
Thr Val Gly Val Ala Lys Lys Glu Val Ile Trp Tyr Pro Leu Leu Gly
            505             510             515

CAA CTA TAT ACA TTA GCC CAT CAT ATT CGT ATA GAT CGG TCA AAC CCG        480
Gln Leu Tyr Thr Leu Ala His His Ile Arg Ile Asp Arg Ser Asn Pro
520             525             530             535

GCT GCG GCT ATT CAG TCT ATG AAA GAG GCA GTT CGT GTA ATA ACC GAA        528
Ala Ala Ala Ile Gln Ser Met Lys Glu Ala Val Arg Val Ile Thr Glu
            540             545             550

AAG AAT CTC TCT CTG ATT ATG TTT CCA GAG GGA ACC AGG TCG GGA GAT        576
Lys Asn Leu Ser Leu Ile Met Phe Pro Glu Gly Thr Arg Ser Gly Asp
            555             560             565

GGG CGT TTA CTT CCT TTC AAG AAG GGT TTT GTT CAT CTA GCA CTT CAG        624
Gly Arg Leu Leu Pro Phe Lys Lys Gly Phe Val His Leu Ala Leu Gln
            570             575             580

TCA CAC CTC CCG ATA GTT CCG ATG ATC CTT ACA GGT ACA CAT TTA GCA        672
Ser His Leu Pro Ile Val Pro Met Ile Leu Thr Gly Thr His Leu Ala
            585             590             595

TGG AGG AAA GGT ACC TTC CGT GTC CGG CCA GTA CCC ATC ACT GTC AAG        720
Trp Arg Lys Gly Thr Phe Arg Val Arg Pro Val Pro Ile Thr Val Lys
600             605             610             615

TAC CTT CCT CCT ATA AAC ACT GAT GAT TGG ACT GTT GAC AAA ATC GAC        768
Tyr Leu Pro Pro Ile Asn Thr Asp Asp Trp Thr Val Asp Lys Ile Asp
            620             625             630

GAT TAC GTC AAA ATG ATA CAC GAC ATC TAT GTC CGC AAC CTA CCT GCG        816
Asp Tyr Val Lys Met Ile His Asp Ile Tyr Val Arg Asn Leu Pro Ala
            635             640             645

TCT CAA AAA CCA CTT GGT AGC ACA AAT CGC TCA AAG TGA GTCGCTCTTT        865
Ser Gln Lys Pro Leu Gly Ser Thr Asn Arg Ser Lys
```

-continued

```
                    650                  655                  660
ACTCCAAGGT TAGCATAATG GATACGTACT TTAGTCTTGC TGCATGAAAA GTTTAATCCT     925

TTCTTGTGAT ATTAGATTAC AGCGTAAGAC TTTCATGTTA AAGTAGTGTA ACAGTGCTTC     985

TTGTTTGTAA CTTTTACAAT AAAAGTACCC TTTTGAAGAA GGGAGCAAGG TTTAAATAGA    1045

AACGAGTTCT AGTTCTTCTC TTGAAAAAAA                                     1075
```

(2) INFORMATION FOR SEQ ID NO: 8:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Lys Thr Arg Thr Ser Ser Leu Arg Asn Arg Arg Gln Leu Lys
 1               5                  10                  15

Pro Ala Val Ala Ala Thr Ala Asp Asp Asp Lys Asp Gly Val Phe Met
             20                  25                  30

Val Leu Leu Ser Cys Phe Lys Ile Phe Val Cys Phe Ala Val Val Leu
         35                  40                  45

Ile Thr Ala Val Ala Trp Gly Leu Ile Met Val Leu Leu Leu Pro Trp
     50                  55                  60

Pro Tyr Met Arg Ile Arg Leu Gly Asn Leu Tyr Gly His Ile Ile Gly
 65                  70                  75                  80

Gly Leu Val Ile Trp Ile Tyr Gly Ile Pro Ile Lys Ile Gln Gly Ser
                 85                  90                  95

Glu His Thr Lys Lys Arg Ala Ile Tyr Ile Ser Asn His Ala Ser Pro
            100                 105                 110

Ile Asp Ala Phe Phe Val Met Trp Leu Ala Pro Ile Gly Thr Val Gly
        115                 120                 125

Val Ala Lys Lys Glu Val Ile Trp Tyr Pro Leu Leu Gly Gln Leu Tyr
    130                 135                 140

Thr Leu Ala His His Ile Arg Ile Asp Arg Ser Asn Pro Ala Ala Ala
145                 150                 155                 160

Ile Gln Ser Met Lys Glu Ala Val Arg Val Ile Thr Glu Lys Asn Leu
                165                 170                 175

Ser Leu Ile Met Phe Pro Glu Gly Thr Arg Ser Gly Asp Gly Arg Leu
            180                 185                 190

Leu Pro Phe Lys Lys Gly Phe Val His Leu Ala Leu Gln Ser His Leu
        195                 200                 205

Pro Ile Val Pro Met Ile Leu Thr Gly Thr His Leu Ala Trp Arg Lys
    210                 215                 220

Gly Thr Phe Arg Val Arg Pro Val Pro Ile Thr Val Lys Tyr Leu Pro
225                 230                 235                 240

Pro Ile Asn Thr Asp Asp Trp Thr Val Asp Lys Ile Asp Asp Tyr Val
                245                 250                 255

Lys Met Ile His Asp Ile Tyr Val Arg Asn Leu Pro Ala Ser Gln Lys
            260                 265                 270

Pro Leu Gly Ser Thr Asn Arg Ser Lys
        275                 280
```

(2) INFORMATION FOR SEQ ID NO: 9:

(i) SEQUENCE CHARACTERISTICS:
    (A) LENGTH: 242 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Escherichia coli
    (B) STRAIN: 2AT (PLSC)

(xi) SEQUENCE DESCRIPTION: SEQ ID NO: 9:

Met Leu Tyr Ile Phe Arg Leu Ile Ile Thr Val Ile Tyr Ser Ile Leu
1               5                   10                  15

Val Cys Val Phe Gly Ser Ile Tyr Cys Leu Phe Ser Pro Arg Asn Pro
            20                  25                  30

Lys His Val Ala Thr Phe Gly His Met Phe Gly Arg Leu Ala Pro Leu
        35                  40                  45

Phe Gly Leu Lys Val Glu Cys Arg Lys Pro Thr Asp Ala Glu Ser Tyr
    50                  55                  60

Gly Asn Ala Ile Tyr Ile Ala Asn His Gln Asn Asn Tyr Asp Met Val
65                  70                  75                  80

Thr Ala Ser Asn Ile Val Gln Pro Pro Thr Val Thr Val Gly Lys Lys
                85                  90                  95

Ser Leu Leu Trp Ile Pro Phe Phe Gly Gln Leu Tyr Trp Leu Thr Gly
            100                 105                 110

Asn Leu Leu Ile Asp Arg Asn Asn Arg Thr Lys Ala His Gly Thr Ile
        115                 120                 125

Ala Glu Val Val Asn His Phe Lys Lys Arg Arg Ile Ser Ile Trp Met
130                 135                 140

Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
            180                 185                 190

Asn Gly Leu Val Ile Val Glu Met Leu Pro Pro Ile Asp Val Ser Gln
        195                 200                 205

Tyr Gly Lys Asp Gln Val Arg Glu Leu Ala Ala His Cys Arg Ser Ile
    210                 215                 220

Met Glu Gln Lys Ile Ala Glu Leu Asp Lys Glu Val Ala Glu Arg Glu
225                 230                 235                 240

Ala Ala (2) INFORMATION FOR SEQ ID NO: 10:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Limnanthes douglasii
        (B) STRAIN: pCB129

(xi) SEQUENCE DESCRIPTION: SEQ ID NO: 10:

Met Val Leu Leu Ser Cys Phe Lys Ile Phe Val Cys Phe Ala Val Val

```
1               5                  10                 15
Leu Ile Thr Ala Val Ala Trp Gly Leu Ile Met Val Leu Leu Leu Pro
                20                 25              30

Trp Pro Tyr Met Arg Ile Arg Leu Gly Asn Leu Tyr Gly His Ile Ile
            35              40              45

Gly Gly Leu Val Ile Trp Ile Tyr Gly Ile Pro Ile Lys Ile Gln Gly
    50              55              60

Ser Glu His Thr Lys Lys Arg Ala Ile Tyr Ile Ser Asn His Ala Ser
65              70              75              80

Pro Ile Asp Ala Phe Phe Val Met Trp Leu Ala Pro Ile Gly Thr Val
                85              90              95

Gly Val Ala Lys Lys Glu Val Ile Trp Tyr Pro Leu Leu Gly Gln Leu
                100             105             110

Tyr Thr Leu Ala His His Ile Arg Ile Asp Arg Ser Asn Pro Ala Ala
            115             120             125

Ala Ile Gln Ser Met Lys Glu Ala Val Arg Val Ile Thr Glu Glu Asn
    130             135             140

Leu Ser Leu Ile Met Phe Pro Glu Gly Thr Arg Ser Gly Asp Gly Arg
145             150             155             160

Leu Leu Pro Phe Lys Lys Gly Phe Val His Leu Ala Leu Gln Ser His
                165             170             175

Leu Pro Ile Val Pro Met Ile Leu Thr Gly Thr His Leu Ala Trp Arg
            180             185             190

Lys Gly Thr Phe Arg Val Arg Pro Val Pro Ile Thr Val Lys Tyr Leu
            195             200             205

Pro Pro Ile Asn Thr Asp Asp Trp Thr Val Asp Lys Ile Asp Asp Tyr
    210             215             220

Val Lys Met Ile His Asp Ile Tyr Val Arg Asn Leu Pro Ala Ser Gln
225             230             235             240

Lys Pro Leu Gly Ser Thr Asn Arg Ser
                245

(2) INFORMATION FOR SEQ ID NO: 11:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli
        (B) STRAIN: 2AT (PLSC)

(xi) SEQUENCE DESCRIPTION: SEQ ID NO: 11:

Ala Ile Tyr Ile Ala Asn His Gln Asn Asn Tyr Asp Met Val Thr Ala
1               5               10              15

Ser Asn Ile Val Gln Pro Pro Thr Val Thr Val Gly Lys Lys Ser Leu
            20              25              30

Leu Trp Ile Pro Phe Phe Gly Gln Leu Tyr Trp Leu Thr Gly Asn Leu
        35              40              45

Leu Ile Asp Arg Asn Asn Arg Thr Lys Ala His Gly Thr Ile Ala Glu
    50              55              60

Val Val Asn His Phe Lys Lys Arg Arg Ile Ser Ile Trp Met Phe Pro
65              70              75              80
```

```
Glu Gly Thr Arg Ser Arg Gly Arg Gly Leu Leu Pro Phe Lys Thr Gly
                85                  90                  95

Ala Phe His Ala Ala Ile Ala Ala Gly Val Pro Ile Ile Pro Val Cys
            100                 105                 110

Val Ser Thr Thr Ser Asn Lys Ile Asn Leu Asn Arg Leu His Asn Gly
            115                 120                 125

Leu Val Ile Val Glu Met Leu Pro Pro Ile Asp
130                 135
```

(2) INFORMATION FOR SEQ ID NO: 12:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Limnanthes douglasii
        (B) STRAIN: pCB129

(xi) SEQUENCE DESCRIPTION: SEQ ID NO: 12:

```
Ala Ile Tyr Ile Ser Asn His Ala Ser Pro Ile Asp Ala Phe Phe Val
1               5                   10                  15

Met Trp Leu Ala Pro Ile Gly Thr Val Gly Val Ala Lys Lys Glu Val
            20                  25                  30

Ile Trp Tyr Pro Leu Leu Gly Gln Leu Tyr Thr Leu Ala His His Ile
            35                  40                  45

Arg Ile Asp Arg Ser Asn Pro Ala Ala Ala Ile Gln Ser Met Lys Glu
50                  55                  60

Ala Val Arg Val Ile Thr Glu Glu Asn Leu Ser Leu Ile Met Phe Pro
65                  70                  75                  80

Glu Gly Thr Arg Ser Gly Asp Gly Arg Leu Leu Pro Phe Lys Lys Gly
                85                  90                  95

Phe Val His Leu Ala Leu Gln Ser His Leu Pro Ile Val Pro Met Ile
            100                 105                 110

Leu Thr Gly Thr His Leu Ala Trp Arg Lys Gly Thr Phe Arg Val Arg
            115                 120                 125

Pro Val Pro Ile Thr Val Lys Tyr Leu Pro Pro Ile Asn
130                 135                 140
```

(2) INFORMATION FOR SEQ ID NO: 13:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Escherichia coli
        (B) STRAIN: 2AT (PLSC)

(xi) SEQUENCE DESCRIPTION: SEQ ID NO: 13:

```
Met Leu Tyr Ile Phe Arg Leu Ile Ile Thr Val Ile Tyr Ser Ile Leu
1               5                   10                  15

Val Cys Val Phe Gly Ser Ile Tyr Cys Leu Phe Ser Pro Arg Asn Pro
            20                  25                  30
```

-continued

```
Lys His Val Ala Thr Phe Gly His Met Phe Gly Arg Leu Ala Pro Leu
    35                  40                  45

Phe Gly Leu Lys Val Glu Cys Arg Lys Pro Thr Asp Ala Glu Ser Tyr
    50                  55                  60

Gly Asn Ala Ile Tyr Ile Ala Asn His Gln Asn Asn Tyr Asp Met Val
65                  70                  75                  80

Thr Ala Ser Asn Ile Val Gln Pro Pro Thr Val Thr Val Gly Lys Lys
            85                  90                  95

Ser Leu Leu Trp Ile Pro Phe Phe Gly Gln Leu Tyr Trp Leu Thr Gly
            100                 105                 110

Asn Leu Leu Ile Asp Arg Asn Asn Arg Thr Lys Ala His Gly Thr Ile
            115                 120                 125

Ala Glu Val Val Asn His Phe Lys Lys Arg Arg Ile Ser Ile Trp Met
    130                 135                 140

Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
            180                 185                 190

Asn Gly Leu Val Ile Val Glu Met Leu Pro Pro Ile Asp Val Ser Gln
        195                 200                 205

Tyr Gly Lys Asp Gln Val Arg Glu Leu Ala Ala His Cys Arg Ser Ile
    210                 215                 220

Met Glu Gln Lys Ile Ala Glu Leu Asp Lys Glu Val Ala Glu Arg Glu
225                 230                 235                 240

Ala Ala Gly Lys Val
            245
```